US 12,403,315 B2

United States Patent
Jayakumar et al.

(10) Patent No.: US 12,403,315 B2
(45) Date of Patent: Sep. 2, 2025

(54) SYSTEMS AND METHODS FOR AUTOMATED PROGRAMMING OF ELECTRICAL STIMULATION

(71) Applicant: Boston Scientific Neuromodulation Corporation, Valencia, CA (US)

(72) Inventors: Adarsh Jayakumar, Valencia, CA (US); Thien Tich Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 429 days.

(21) Appl. No.: 17/728,493

(22) Filed: Apr. 25, 2022

(65) Prior Publication Data

US 2022/0339448 A1  Oct. 27, 2022

Related U.S. Application Data

(60) Provisional application No. 63/180,380, filed on Apr. 27, 2021.

(51) Int. Cl.
*A61N 1/36* (2006.01)
*A61N 1/372* (2006.01)

(52) U.S. Cl.
CPC ..... *A61N 1/36139* (2013.01); *A61N 1/37247* (2013.01)

(58) Field of Classification Search
CPC .. A61N 1/36139; A61N 1/37247; A61N 1/36; A61N 1/36146; A61N 1/36135
See application file for complete search history.

(56) References Cited

U.S. PATENT DOCUMENTS 3,999,555 A  12/1976  Person
4,144,889 A  3/1979  Tyers et al.
(Continued)

FOREIGN PATENT DOCUMENTS

EP  813889  12/1997
EP  1048320  11/2000
(Continued)

OTHER PUBLICATIONS

Zhang, Y., et al., "Atlas-guided tract reconstruction for automated and comprehensive examination of the white matter anatomy," Neuroimage 52(4) (2010), pp. 1289-1301.
(Continued)

*Primary Examiner* — Niketa Patel
*Assistant Examiner* — Attiya Sayyada Hussaini
(74) *Attorney, Agent, or Firm* — Branch Partners PLLC; Bruce E. Black

(57) ABSTRACT

A method for automating selection of stimulation parameters for a stimulation device implanted in a patient includes setting, by a user, at least one limit on each of at least one stimulation parameter and performing, automatically using at least one processor, the following actions for each of a plurality of sets of the stimulation parameters constrained by the at least one limit: stimulating the patient, by the stimulation device, using the set of stimulation parameters, sensing one or more effects arising in response to the stimulation, and updating, by the at least one processor, a collection of the effects and sets of stimulation parameters with the one or more effects and the set of stimulation parameters. The method further includes selecting, by the processor, one of the sets of stimulation parameters based on the effects.

18 Claims, 7 Drawing Sheets

(56) References Cited

U.S. PATENT DOCUMENTS

| | | |
|---|---|---|
| 4,177,818 A | 12/1979 | De Pedro |
| 4,341,221 A | 7/1982 | Testerman |
| 4,378,797 A | 4/1983 | Osterholm |
| 4,445,500 A | 5/1984 | Osterholm |
| 4,735,208 A | 4/1988 | Wyler et al. |
| 4,765,341 A | 8/1988 | Mower et al. |
| 4,841,973 A | 6/1989 | Stecker |
| 5,067,495 A | 11/1991 | Brehm |
| 5,099,846 A | 3/1992 | Hardy |
| 5,222,494 A | 6/1993 | Baker, Jr. |
| 5,255,693 A | 10/1993 | Dutcher |
| 5,259,387 A | 11/1993 | dePinto |
| 5,304,206 A | 4/1994 | Baker, Jr. et al. |
| 5,344,438 A | 9/1994 | Testerman et al. |
| 5,361,763 A | 11/1994 | Kao et al. |
| 5,452,407 A | 9/1995 | Crook |
| 5,560,360 A | 10/1996 | Filler et al. |
| 5,565,949 A | 10/1996 | Kasha, Jr. |
| 5,593,427 A | 1/1997 | Gliner et al. |
| 5,601,612 A | 2/1997 | Gliner et al. |
| 5,607,454 A | 3/1997 | Cameron et al. |
| 5,620,470 A | 4/1997 | Gliner et al. |
| 5,651,767 A | 7/1997 | Schulman |
| 5,711,316 A | 1/1998 | Elsberry et al. |
| 5,713,922 A | 2/1998 | King |
| 5,716,377 A | 2/1998 | Rise et al. |
| 5,724,985 A | 3/1998 | Snell et al. |
| 5,749,904 A | 5/1998 | Gliner et al. |
| 5,749,905 A | 5/1998 | Gliner et al. |
| 5,776,170 A | 7/1998 | MacDonald et al. |
| 5,782,762 A | 7/1998 | Vining |
| 5,843,148 A | 12/1998 | Gijsbers et al. |
| 5,859,922 A | 1/1999 | Hoffmann |
| 5,868,740 A | 2/1999 | LeVeen et al. |
| 5,897,583 A | 4/1999 | Meyer et al. |
| 5,910,804 A | 6/1999 | Fortenbery et al. |
| 5,925,070 A | 7/1999 | King et al. |
| 5,938,688 A | 8/1999 | Schiff |
| 5,938,690 A | 8/1999 | Law et al. |
| 5,978,713 A | 11/1999 | Prutchi et al. |
| 6,016,449 A | 1/2000 | Fischell et al. |
| 6,029,090 A | 2/2000 | Herbst |
| 6,029,091 A | 2/2000 | de la Rama et al. |
| 6,050,992 A | 4/2000 | Nichols |
| 6,058,331 A | 5/2000 | King |
| 6,066,163 A | 5/2000 | John |
| 6,080,187 A | 6/2000 | Alt et al. |
| 6,083,162 A | 7/2000 | Vining |
| 6,094,598 A | 7/2000 | Elsberry et al. |
| 6,096,756 A | 8/2000 | Crain et al. |
| 6,106,460 A | 8/2000 | Panescu et al. |
| 6,109,269 A | 8/2000 | Rise et al. |
| 6,128,538 A | 10/2000 | Fischell et al. |
| 6,129,685 A | 10/2000 | Howard, III |
| 6,146,390 A | 11/2000 | Heilbrun et al. |
| 6,161,044 A | 12/2000 | Silverstone |
| 6,167,311 A | 12/2000 | Rezai |
| 6,181,969 B1 | 1/2001 | Gord |
| 6,192,266 B1 | 2/2001 | Dupree et al. |
| 6,205,361 B1 | 3/2001 | Kuzma |
| 6,208,881 B1 | 3/2001 | Champeau |
| 6,240,308 B1 | 5/2001 | Hardy et al. |
| 6,246,912 B1 | 6/2001 | Sluijter et al. |
| 6,253,109 B1 | 6/2001 | Gielen |
| 6,289,239 B1 | 9/2001 | Panescu et al. |
| 6,301,492 B1 | 10/2001 | Zonenshayn |
| 6,310,619 B1 | 10/2001 | Rice |
| 6,319,241 B1 | 11/2001 | King |
| 6,336,899 B1 | 1/2002 | Yamazaki |
| 6,343,226 B1 | 1/2002 | Sunde et al. |
| 6,351,675 B1 | 2/2002 | Tholen et al. |
| 6,353,762 B1 | 3/2002 | Baudino et al. |
| 6,366,813 B1 | 4/2002 | Dilorenzo |
| 6,368,331 B1 | 4/2002 | Front et al. |
| 6,389,311 B1 | 5/2002 | Whayne et al. |
| 6,393,325 B1 | 5/2002 | Mann et al. |
| 6,421,566 B1 | 7/2002 | Holsheimer |
| 6,435,878 B1 | 8/2002 | Reynolds et al. |
| 6,442,432 B2 | 8/2002 | Lee |
| 6,463,328 B1 | 10/2002 | John |
| 6,491,699 B1 | 12/2002 | Henderson et al. |
| 6,494,831 B1 | 12/2002 | Koritzinsky |
| 6,507,759 B1 | 1/2003 | Prutchi et al. |
| 6,510,347 B2 | 1/2003 | Borkan |
| 6,516,227 B1 | 2/2003 | Meadows et al. |
| 6,517,480 B1 | 2/2003 | Krass |
| 6,539,263 B1 | 3/2003 | Schiff |
| 6,560,490 B2 | 5/2003 | Grill et al. |
| 6,579,280 B1 | 6/2003 | Kovach et al. |
| 6,600,956 B2 | 7/2003 | Maschino et al. |
| 6,606,523 B1 | 8/2003 | Jenkins |
| 6,609,029 B1 | 8/2003 | Mann et al. |
| 6,609,031 B1 | 8/2003 | Law et al. |
| 6,609,032 B1 | 8/2003 | Woods et al. |
| 6,622,048 B1 | 9/2003 | Mann et al. |
| 6,631,297 B1 | 10/2003 | Mo |
| 6,654,642 B2 | 11/2003 | North et al. |
| 6,662,053 B2 | 12/2003 | Borkan |
| 6,675,046 B2 | 1/2004 | Holsheimer |
| 6,684,106 B2 | 1/2004 | Herbst |
| 6,687,392 B1 | 2/2004 | Touzawa et al. |
| 6,690,972 B2 | 2/2004 | Conley et al. |
| 6,690,974 B2 | 2/2004 | Archer et al. |
| 6,692,315 B1 | 2/2004 | Soumillion et al. |
| 6,694,162 B2 | 2/2004 | Hartlep |
| 6,694,163 B1 | 2/2004 | Vining |
| 6,708,096 B1 | 3/2004 | Frei et al. |
| 6,741,892 B1 | 5/2004 | Meadows et al. |
| 6,748,098 B1 | 6/2004 | Rosenfeld |
| 6,748,276 B1 | 6/2004 | Daignault, Jr. et al. |
| 6,778,846 B1 | 8/2004 | Martinez et al. |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,845,267 B2 | 1/2005 | Harrison et al. |
| 6,850,802 B2 | 2/2005 | Holsheimer |
| 6,895,280 B2 | 5/2005 | Meadows et al. |
| 6,909,913 B2 | 6/2005 | Vining |
| 6,937,891 B2 | 8/2005 | Leinders et al. |
| 6,937,903 B2 | 8/2005 | Schuler et al. |
| 6,944,497 B2 | 9/2005 | Stypulkowski |
| 6,944,501 B1 | 9/2005 | Pless |
| 6,950,707 B2 | 9/2005 | Whitehurst |
| 6,969,388 B2 | 11/2005 | Goldman et al. |
| 6,993,384 B2 | 1/2006 | Bradley et al. |
| 7,003,349 B1 | 2/2006 | Andersson et al. |
| 7,003,352 B1 | 2/2006 | Whitehurst |
| 7,008,370 B2 | 3/2006 | Tanner et al. |
| 7,008,413 B2 | 3/2006 | Kovach et al. |
| 7,035,690 B2 | 4/2006 | Goetz |
| 7,043,293 B1 | 5/2006 | Baura |
| 7,047,082 B1 | 5/2006 | Schrom et al. |
| 7,047,084 B2 | 5/2006 | Erickson et al. |
| 7,050,857 B2 | 5/2006 | Samuelsson et al. |
| 7,054,692 B1 | 5/2006 | Whitehurst et al. |
| 7,058,446 B2 | 6/2006 | Schuler et al. |
| 7,082,333 B1 | 7/2006 | Bauhahn et al. |
| 7,107,102 B2 | 9/2006 | Daignault et al. |
| 7,126,000 B2 | 10/2006 | Ogawa et al. |
| 7,127,297 B2 | 10/2006 | Law et al. |
| 7,136,518 B2 | 11/2006 | Griffin et al. |
| 7,136,695 B2 | 11/2006 | Pless et al. |
| 7,142,923 B2 | 11/2006 | North et al. |
| 7,146,219 B2 | 12/2006 | Sieracki et al. |
| 7,146,223 B1 | 12/2006 | King |
| 7,151,961 B1 | 12/2006 | Whitehurst |
| 7,155,279 B2 | 12/2006 | Whitehurst |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,191,014 B2 | 3/2007 | Kobayashi et al. |
| 7,209,787 B2 | 4/2007 | Dilorenzo |

(56) References Cited

U.S. PATENT DOCUMENTS

| | | |
|---|---|---|
| 7,211,050 B1 | 5/2007 | Caplygin |
| 7,216,000 B2 | 5/2007 | Sieracki et al. |
| 7,217,276 B2 | 5/2007 | Henderson |
| 7,218,968 B2 | 5/2007 | Condie et al. |
| 7,228,179 B2 | 6/2007 | Campen et al. |
| 7,231,254 B2 | 6/2007 | DiLorenzo |
| 7,236,830 B2 | 6/2007 | Gliner |
| 7,239,910 B2 | 7/2007 | Tanner |
| 7,239,916 B2 | 7/2007 | Thompson et al. |
| 7,239,926 B2 | 7/2007 | Goetz |
| 7,242,984 B2 | 7/2007 | DiLorenzo |
| 7,244,150 B1 | 7/2007 | Brase et al. |
| 7,252,090 B2 | 8/2007 | Goetz |
| 7,254,445 B2 | 8/2007 | Law et al. |
| 7,254,446 B1 | 8/2007 | Erickson |
| 7,257,447 B2 | 8/2007 | Cates et al. |
| 7,266,412 B2 | 9/2007 | Stypulkowski |
| 7,289,761 B2 | 10/2007 | Mazar et al. |
| 7,294,107 B2 | 11/2007 | Simon et al. |
| 7,295,876 B1 | 11/2007 | Erickson |
| 7,299,096 B2 | 11/2007 | Balzer et al. |
| 7,308,302 B1 | 12/2007 | Schuler et al. |
| 7,313,430 B2 | 12/2007 | Urquhart |
| 7,324,851 B1 | 1/2008 | DiLorenzo |
| 7,346,282 B2 | 3/2008 | Sakanaka et al. |
| 7,346,382 B2 | 3/2008 | McIntyre et al. |
| 7,385,443 B1 | 6/2008 | Denison |
| 7,388,974 B2 | 6/2008 | Yanagita |
| 7,437,193 B2 | 10/2008 | Parramon et al. |
| 7,450,997 B1 | 11/2008 | Pianca et al. |
| 7,454,245 B2 | 11/2008 | Armstrong et al. |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,565,199 B2 | 7/2009 | Sheffield et al. |
| 7,603,177 B2 | 10/2009 | Sieracki et al. |
| 7,617,002 B2 | 11/2009 | Goetz |
| 7,623,918 B2 | 11/2009 | Goetz |
| 7,650,184 B2 | 1/2010 | Walter |
| 7,657,319 B2 | 2/2010 | Goetz et al. |
| 7,672,734 B2 | 3/2010 | Anderson et al. |
| 7,676,273 B2 | 3/2010 | Goetz et al. |
| 7,680,526 B2 | 3/2010 | McIntyre et al. |
| 7,734,340 B2 | 6/2010 | De Ridder |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,826,902 B2 | 11/2010 | Stone et al. |
| 7,848,802 B2 | 12/2010 | Goetz et al. |
| 7,860,548 B2 | 12/2010 | McIntyre et al. |
| 7,896,808 B1 | 3/2011 | Koh et al. |
| 7,904,134 B2 | 3/2011 | McIntyre et al. |
| 7,945,105 B1 | 5/2011 | Jaenisch |
| 7,949,395 B2 | 5/2011 | Kuzma |
| 7,974,706 B2 | 7/2011 | Moffitt et al. |
| 8,000,794 B2 | 8/2011 | Lozano |
| 8,019,439 B2 | 9/2011 | Kuzma et al. |
| 8,019,443 B2 | 9/2011 | Schleicher et al. |
| 8,175,710 B2 | 5/2012 | He |
| 8,180,601 B2 | 5/2012 | Butson et al. |
| 8,187,209 B1 | 5/2012 | Giuffrida |
| 8,195,300 B2 | 6/2012 | Gliner et al. |
| 8,209,027 B2 | 6/2012 | Butson et al. |
| 8,224,450 B2 | 7/2012 | Brase |
| 8,257,684 B2 | 9/2012 | Covalin et al. |
| 8,262,714 B2 | 9/2012 | Hulvershorn et al. |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,306,627 B2 | 11/2012 | Armstrong |
| 8,326,433 B2 | 12/2012 | Blum et al. |
| 8,359,107 B2 | 1/2013 | Pianca et al. |
| 8,364,278 B2 | 1/2013 | Pianca et al. |
| 8,369,954 B2 | 2/2013 | Stack et al. |
| 8,379,952 B2 | 2/2013 | McIntyre et al. |
| 8,391,985 B2 | 3/2013 | McDonald |
| 8,412,349 B2 | 4/2013 | Barker |
| 8,429,174 B2 | 4/2013 | Ramani et al. |
| 8,452,415 B2 | 5/2013 | Goetz et al. |
| 8,467,883 B2 | 6/2013 | Chen et al. |
| 8,473,061 B2 | 6/2013 | Moffitt et al. |
| 8,483,237 B2 | 7/2013 | Zimmermann et al. |
| 8,543,189 B2 | 9/2013 | Paitel et al. |
| 8,571,665 B2 | 10/2013 | Moffitt et al. |
| 8,589,316 B2 | 11/2013 | Lujan et al. |
| 8,594,800 B2 | 11/2013 | Butson et al. |
| 8,594,801 B2 | 11/2013 | Corndorf et al. |
| 8,606,360 B2 | 12/2013 | Butson et al. |
| 8,620,452 B2 | 12/2013 | King et al. |
| 8,649,845 B2 | 2/2014 | McIntyre et al. |
| 8,675,945 B2 | 3/2014 | Barnhorst et al. |
| 8,679,038 B1 | 3/2014 | Giuffrida |
| 8,688,235 B1 | 4/2014 | Pianca et al. |
| 8,744,596 B2 | 6/2014 | Howard |
| 8,751,008 B2 | 6/2014 | Carlton et al. |
| 8,751,016 B2 | 6/2014 | Schleicher et al. |
| 8,774,941 B2 | 7/2014 | Pianca |
| 8,792,993 B2 | 7/2014 | Pianca et al. |
| 8,831,731 B2 | 9/2014 | Blum et al. |
| 8,831,742 B2 | 9/2014 | Pianca et al. |
| 8,845,557 B1 | 9/2014 | Giuffrida et al. |
| 8,849,632 B2 | 9/2014 | Sparks et al. |
| 8,855,773 B2 | 10/2014 | Kokones et al. |
| 8,868,199 B2 | 10/2014 | Kaula et al. |
| 8,913,804 B2 | 12/2014 | Blum et al. |
| 8,918,183 B2 | 12/2014 | Carlton et al. |
| 8,918,184 B1 | 12/2014 | Torgerson et al. |
| 8,923,976 B2 | 12/2014 | Johanek |
| 8,936,622 B2 | 1/2015 | Wales et al. |
| 8,958,615 B2 | 2/2015 | Blum et al. |
| 8,972,023 B2 | 3/2015 | Bradley et al. |
| 8,986,382 B2 | 3/2015 | Bentley et al. |
| 9,020,789 B2 | 4/2015 | Butson et al. |
| 9,026,317 B2 | 5/2015 | Furukawa et al. |
| 9,039,740 B2 | 5/2015 | Wales et al. |
| 9,050,470 B2 | 6/2015 | Carlton et al. |
| 9,061,138 B2 | 6/2015 | Pianca |
| 9,072,905 B2 | 7/2015 | Kokones et al. |
| 9,081,488 B2 | 7/2015 | Soederstroem |
| 9,084,896 B2 | 7/2015 | Kokones et al. |
| 9,135,400 B2 | 9/2015 | McIntyre et al. |
| 9,149,630 B2 | 10/2015 | Howard et al. |
| 9,162,056 B2 | 10/2015 | Pianca |
| 9,220,889 B2 | 12/2015 | Carlton et al. |
| 9,227,074 B2 | 1/2016 | Carcieri et al. |
| 9,235,685 B2 | 1/2016 | McIntyre et al. |
| 9,248,272 B2 | 2/2016 | Romero |
| 9,248,296 B2 | 2/2016 | Carcieri et al. |
| 9,254,387 B2 | 2/2016 | Blum et al. |
| 9,272,153 B2 | 3/2016 | Blum et al. |
| 9,289,596 B2 | 3/2016 | Leven |
| 9,289,600 B2 | 3/2016 | Govea et al. |
| 9,302,110 B2 | 4/2016 | Kokones et al. |
| 9,308,372 B2 | 4/2016 | Sparks et al. |
| 9,310,985 B2 | 4/2016 | Blum et al. |
| 9,327,111 B2 | 5/2016 | Pianca et al. |
| 9,358,398 B2 | 6/2016 | Moffitt et al. |
| 9,364,665 B2 | 6/2016 | Bokil et al. |
| 9,381,348 B2 | 7/2016 | Romero et al. |
| 9,387,325 B1 | 7/2016 | Min et al. |
| 9,415,154 B2 | 8/2016 | Leven |
| 9,474,903 B2 | 10/2016 | Chen et al. |
| 9,492,655 B2 | 11/2016 | Pianca et al. |
| 9,498,620 B2 | 11/2016 | Romero et al. |
| 9,526,898 B2 * | 12/2016 | Libbus ................ A61N 1/0551 |
| 9,526,902 B2 | 12/2016 | Blum et al. |
| 9,533,141 B2 | 1/2017 | Black et al. |
| 9,566,596 B2 | 2/2017 | Kim et al. |
| 9,572,982 B2 | 2/2017 | Burnes et al. |
| 9,586,053 B2 | 3/2017 | Moffitt et al. |
| 9,592,389 B2 | 3/2017 | Moffitt |
| 9,610,435 B2 | 4/2017 | Schleicher et al. |

(56) References Cited

U.S. PATENT DOCUMENTS

| | | |
|---|---|---|
| 9,636,498 B2 | 5/2017 | Leven |
| 9,649,489 B2 | 5/2017 | Wechter et al. |
| 9,669,210 B2 | 6/2017 | Barker et al. |
| 9,713,720 B2 | 7/2017 | Zhu |
| 9,775,988 B2 | 10/2017 | Govea et al. |
| 9,792,412 B2 | 10/2017 | Moffitt et al. |
| 9,821,167 B2 | 11/2017 | Carcieri et al. |
| 9,887,470 B2 | 2/2018 | Nguyen-Stella et al. |
| 9,925,382 B2 | 3/2018 | Carlton et al. |
| 9,959,940 B2 | 5/2018 | Moffitt et al. |
| 9,974,959 B2 | 5/2018 | Moffitt et al. |
| 9,987,482 B2 | 6/2018 | Nageri et al. |
| 10,067,659 B2 | 9/2018 | Bokil |
| 10,071,242 B2 | 9/2018 | Leven |
| 10,071,249 B2 | 9/2018 | Zottola |
| 10,086,205 B2 | 10/2018 | Grill et al. |
| 10,213,148 B2 | 2/2019 | Min et al. |
| 10,226,616 B2 | 3/2019 | Barker |
| 10,265,528 B2 | 4/2019 | Carcieri et al. |
| 10,265,531 B2 | 4/2019 | Bokil |
| 10,286,205 B2 | 5/2019 | Steinke et al. |
| 10,300,282 B2 | 5/2019 | Torgerson et al. |
| 10,335,607 B2 | 7/2019 | Orinski |
| 10,357,657 B2 | 7/2019 | Moffitt et al. |
| 10,369,364 B2 | 8/2019 | Moffitt et al. |
| 10,406,353 B2 | 9/2019 | Wechter |
| 10,485,969 B2 | 11/2019 | Govea et al. |
| 10,493,269 B2 | 12/2019 | Stoffregen et al. |
| 10,525,257 B2 | 1/2020 | Govea et al. |
| 10,525,266 B2 | 1/2020 | Moffitt et al. |
| 10,603,498 B2 | 3/2020 | Blum et al. |
| 10,625,072 B2 | 4/2020 | Serrano Carmona |
| 10,631,937 B2 | 4/2020 | Tyulmankov et al. |
| 10,639,488 B2 | 5/2020 | Kalgren et al. |
| 10,653,330 B2 | 5/2020 | Angle et al. |
| 10,675,468 B2 | 6/2020 | Torgerson |
| 10,709,886 B2 | 7/2020 | Nagaoka et al. |
| 10,716,505 B2 | 7/2020 | Blum et al. |
| 10,780,282 B2 | 9/2020 | Mustakos et al. |
| 10,814,127 B2 | 10/2020 | Nageri et al. |
| 10,814,140 B2 | 10/2020 | Zhang et al. |
| 10,835,739 B2 | 11/2020 | Sandhu |
| 10,850,101 B2 | 12/2020 | Zhang et al. |
| 10,857,351 B2 | 12/2020 | Wang et al. |
| 10,960,203 B2 | 3/2021 | Tyler et al. |
| 11,020,052 B2 | 6/2021 | Zuckerman-Stark et al. |
| 11,285,329 B2 | 3/2022 | Carcieri et al. |
| 11,298,550 B2 | 4/2022 | Howard et al. |
| 11,357,986 B2 | 6/2022 | Steinke et al. |
| 11,517,755 B2 | 12/2022 | Zhang et al. |
| 11,529,510 B2 | 12/2022 | Leven |
| 11,707,622 B2 | 7/2023 | Juarez Paz et al. |
| 11,745,010 B2 | 9/2023 | Donega et al. |
| 2001/0031071 A1 | 10/2001 | Nichols et al. |
| 2002/0032375 A1 | 3/2002 | Bauch et al. |
| 2002/0062143 A1 | 5/2002 | Baudino et al. |
| 2002/0087201 A1 | 7/2002 | Firlik et al. |
| 2002/0099295 A1 | 7/2002 | Gil et al. |
| 2002/0115603 A1 | 8/2002 | Whitehouse |
| 2002/0116030 A1 | 8/2002 | Rezei |
| 2002/0123780 A1 | 9/2002 | Grill et al. |
| 2002/0128694 A1 | 9/2002 | Holsheimer |
| 2002/0151939 A1 | 10/2002 | Rezai |
| 2002/0183607 A1 | 12/2002 | Bauch et al. |
| 2002/0183740 A1 | 12/2002 | Edwards et al. |
| 2002/0183817 A1 | 12/2002 | Van Venrooij et al. |
| 2003/0097159 A1 | 5/2003 | Schiff et al. |
| 2003/0149450 A1 | 8/2003 | Mayberg |
| 2003/0171791 A1 | 9/2003 | KenKnight et al. |
| 2003/0212439 A1 | 11/2003 | Schuler et al. |
| 2004/0034394 A1 | 2/2004 | Woods et al. |
| 2004/0044279 A1 | 3/2004 | Lewin et al. |
| 2004/0044378 A1 | 3/2004 | Holsheimer |
| 2004/0044379 A1 | 3/2004 | Holsheimer |
| 2004/0054297 A1* | 3/2004 | Wingeier ............ A61B 5/165 600/544 |
| 2004/0059395 A1 | 3/2004 | North et al. |
| 2004/0106916 A1 | 6/2004 | Quaid et al. |
| 2004/0133248 A1 | 7/2004 | Frei et al. |
| 2004/0152957 A1 | 8/2004 | Stivoric et al. |
| 2004/0181262 A1 | 9/2004 | Bauhahn |
| 2004/0186532 A1 | 9/2004 | Tadlock |
| 2004/0193231 A1 | 9/2004 | David et al. |
| 2004/0199216 A1 | 10/2004 | Lee et al. |
| 2004/0267330 A1 | 12/2004 | Lee et al. |
| 2005/0021090 A1 | 1/2005 | Schuler et al. |
| 2005/0033380 A1 | 2/2005 | Tanner et al. |
| 2005/0049649 A1 | 3/2005 | Luders et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0075689 A1 | 4/2005 | Toy et al. |
| 2005/0085714 A1 | 4/2005 | Foley et al. |
| 2005/0165294 A1 | 7/2005 | Weiss |
| 2005/0171587 A1 | 8/2005 | Daglow et al. |
| 2005/0228250 A1 | 10/2005 | Bitter et al. |
| 2005/0251061 A1 | 11/2005 | Schuler et al. |
| 2005/0261061 A1 | 11/2005 | Nguyen et al. |
| 2005/0261601 A1 | 11/2005 | Schuler et al. |
| 2005/0261747 A1 | 11/2005 | Schuler et al. |
| 2005/0267347 A1 | 12/2005 | Oster |
| 2005/0288732 A1 | 12/2005 | Schuler et al. |
| 2006/0004422 A1 | 1/2006 | De Ridder |
| 2006/0017749 A1 | 1/2006 | McIntyre et al. |
| 2006/0020292 A1 | 1/2006 | Goetz et al. |
| 2006/0069415 A1 | 3/2006 | Cameron et al. |
| 2006/0094951 A1 | 5/2006 | Dean et al. |
| 2006/0095088 A1 | 5/2006 | Riddler |
| 2006/0155340 A1 | 7/2006 | Schuler et al. |
| 2006/0206169 A1 | 9/2006 | Schuler |
| 2006/0218007 A1 | 9/2006 | Bjorner et al. |
| 2006/0224189 A1 | 10/2006 | Schuler et al. |
| 2006/0235472 A1 | 10/2006 | Goetz et al. |
| 2006/0259079 A1 | 11/2006 | King |
| 2006/0259099 A1 | 11/2006 | Goetz et al. |
| 2007/0000372 A1 | 1/2007 | Rezai et al. |
| 2007/0017749 A1 | 1/2007 | Dold et al. |
| 2007/0027499 A1 | 2/2007 | Maschino et al. |
| 2007/0027514 A1 | 2/2007 | Gerber |
| 2007/0043268 A1 | 2/2007 | Russell |
| 2007/0049817 A1 | 3/2007 | Preiss et al. |
| 2007/0067003 A1 | 3/2007 | Sanchez et al. |
| 2007/0078498 A1 | 4/2007 | Rezai et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0135855 A1 | 6/2007 | Foshee et al. |
| 2007/0150026 A1 | 6/2007 | Bourget et al. |
| 2007/0150036 A1 | 6/2007 | Anderson |
| 2007/0156186 A1 | 7/2007 | Lee et al. |
| 2007/0162086 A1 | 7/2007 | DiLorenzo |
| 2007/0162235 A1 | 7/2007 | Zhan et al. |
| 2007/0168004 A1 | 7/2007 | Walter |
| 2007/0168007 A1 | 7/2007 | Kuzma et al. |
| 2007/0179557 A1 | 8/2007 | Maschino et al. |
| 2007/0185544 A1 | 8/2007 | Dawant et al. |
| 2007/0191887 A1 | 8/2007 | Schuler et al. |
| 2007/0191912 A1 | 8/2007 | Ficher et al. |
| 2007/0197891 A1 | 8/2007 | Shachar et al. |
| 2007/0203450 A1 | 8/2007 | Berry |
| 2007/0203532 A1 | 8/2007 | Tass et al. |
| 2007/0203537 A1 | 8/2007 | Goetz et al. |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1* | 8/2007 | Goetz ............ A61N 1/37247 607/59 |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |

(56) References Cited

U.S. PATENT DOCUMENTS

| | | |
|---|---|---|
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0260283 A1 | 11/2007 | Li |
| 2007/0265664 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0039895 A1 | 2/2008 | Fowler et al. |
| 2008/0046037 A1 | 2/2008 | Haubrich et al. |
| 2008/0071150 A1 | 3/2008 | Miesel et al. |
| 2008/0081982 A1 | 4/2008 | Simon et al. |
| 2008/0086451 A1 | 4/2008 | Torres et al. |
| 2008/0091248 A1 | 4/2008 | Libbus et al. |
| 2008/0103533 A1 | 5/2008 | Patel et al. |
| 2008/0114233 A1 | 5/2008 | McIntyre et al. |
| 2008/0114579 A1 | 5/2008 | McIntyre et al. |
| 2008/0123922 A1 | 5/2008 | Gielen et al. |
| 2008/0123923 A1 | 5/2008 | Gielen et al. |
| 2008/0133141 A1 | 6/2008 | Frost |
| 2008/0141217 A1 | 6/2008 | Goetz et al. |
| 2008/0154340 A1 | 6/2008 | Goetz et al. |
| 2008/0154341 A1 | 6/2008 | McIntyre et al. |
| 2008/0163097 A1 | 7/2008 | Goetz et al. |
| 2008/0183256 A1 | 7/2008 | Keacher |
| 2008/0188734 A1 | 8/2008 | Suryanarayanan et al. |
| 2008/0215101 A1 | 9/2008 | Rezai et al. |
| 2008/0215118 A1 | 9/2008 | Goetz et al. |
| 2008/0227139 A1 | 9/2008 | Deisseroth et al. |
| 2008/0238749 A1 | 10/2008 | Comdorf |
| 2008/0242950 A1 | 10/2008 | Jung et al. |
| 2008/0261165 A1 | 10/2008 | Steingart et al. |
| 2008/0269588 A1 | 10/2008 | Csavoy et al. |
| 2008/0300654 A1 | 12/2008 | Lambert et al. |
| 2008/0300797 A1 | 12/2008 | Tabibiazar et al. |
| 2009/0016491 A1 | 1/2009 | Li |
| 2009/0054947 A1 | 2/2009 | Bourn et al. |
| 2009/0054950 A1 | 2/2009 | Stephens |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0118635 A1 | 5/2009 | Lujan et al. |
| 2009/0118786 A1 | 5/2009 | Meadows et al. |
| 2009/0149917 A1 | 6/2009 | Whitehurst et al. |
| 2009/0163975 A1 | 6/2009 | Gerber et al. |
| 2009/0187222 A1 | 7/2009 | Barker |
| 2009/0196471 A1 | 8/2009 | Goetz et al. |
| 2009/0196472 A1 | 8/2009 | Goetz et al. |
| 2009/0198306 A1 | 8/2009 | Goetz et al. |
| 2009/0198354 A1 | 8/2009 | Wilson |
| 2009/0204192 A1 | 8/2009 | Carlton et al. |
| 2009/0208073 A1 | 8/2009 | McIntyre et al. |
| 2009/0210208 A1 | 8/2009 | McIntyre et al. |
| 2009/0228073 A1 | 9/2009 | Scholten |
| 2009/0242399 A1 | 10/2009 | Kamath et al. |
| 2009/0270949 A1 | 10/2009 | Kalpin et al. |
| 2009/0276008 A1 | 11/2009 | Lee et al. |
| 2009/0276021 A1 | 11/2009 | Meadows et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010387 A1 | 1/2010 | Skelton et al. |
| 2010/0010432 A1 | 1/2010 | Skelton |
| 2010/0010566 A1 | 1/2010 | Thacker et al. |
| 2010/0010646 A1 | 1/2010 | Drew et al. |
| 2010/0023103 A1 | 1/2010 | Elborno |
| 2010/0023130 A1 | 1/2010 | Henry et al. |
| 2010/0030312 A1 | 2/2010 | Shen |
| 2010/0049276 A1 | 2/2010 | Blum et al. |
| 2010/0049280 A1 | 2/2010 | Goetz |
| 2010/0057161 A1 | 3/2010 | Machado et al. |
| 2010/0064249 A1 | 3/2010 | Groetken |
| 2010/0076535 A1 | 3/2010 | Pianca et al. |
| 2010/0113959 A1 | 5/2010 | Pascual-Leon et al. |
| 2010/0121409 A1 | 5/2010 | Kothandaraman et al. |
| 2010/0135553 A1 | 6/2010 | Joglekar |
| 2010/0137944 A1 | 6/2010 | Zhu |
| 2010/0152604 A1 | 6/2010 | Kuala et al. |
| 2010/0152807 A1 | 6/2010 | Grill et al. |
| 2010/0179562 A1 | 7/2010 | Linker et al. |
| 2010/0211135 A1 | 8/2010 | Caparso et al. |
| 2010/0268298 A1 | 10/2010 | Moffitt |
| 2010/0324410 A1 | 12/2010 | Paek et al. |
| 2010/0331883 A1 | 12/2010 | Schmitz et al. |
| 2011/0004267 A1 | 1/2011 | Meadows |
| 2011/0005069 A1 | 1/2011 | Pianca |
| 2011/0040351 A1 | 2/2011 | Buston et al. |
| 2011/0054559 A1 | 3/2011 | Rosenberg et al. |
| 2011/0066407 A1 | 3/2011 | Butson et al. |
| 2011/0078900 A1 | 4/2011 | Pianca et al. |
| 2011/0093045 A1 | 4/2011 | Moffitt |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0137372 A1 | 6/2011 | Makous et al. |
| 2011/0160796 A1 | 6/2011 | Lane et al. |
| 2011/0172737 A1 | 7/2011 | Davis et al. |
| 2011/0184487 A1 | 7/2011 | Alberts et al. |
| 2011/0191275 A1 | 8/2011 | Lujan et al. |
| 2011/0196253 A1 | 8/2011 | McIntyre et al. |
| 2011/0213440 A1 | 9/2011 | Fowler et al. |
| 2011/0224665 A1 | 9/2011 | Crosby et al. |
| 2011/0224680 A1 | 9/2011 | Barker |
| 2011/0238129 A1 | 9/2011 | Moffitt |
| 2011/0251583 A1 | 10/2011 | Miyazawa et al. |
| 2011/0270348 A1 | 11/2011 | Goetz |
| 2011/0306845 A1 | 12/2011 | Osorio |
| 2011/0306846 A1 | 12/2011 | Osorio |
| 2011/0307032 A1 | 12/2011 | Goetz et al. |
| 2011/0313485 A1 | 12/2011 | DeMulling et al. |
| 2011/0313500 A1 | 12/2011 | Barker et al. |
| 2012/0016378 A1 | 1/2012 | Pianca et al. |
| 2012/0027272 A1 | 2/2012 | Akinyemi et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0078106 A1 | 3/2012 | Dentinger et al. |
| 2012/0089205 A1 | 4/2012 | Boyden et al. |
| 2012/0101552 A1 | 4/2012 | Lazarewicz et al. |
| 2012/0116476 A1 | 5/2012 | Kothandaraman |
| 2012/0165898 A1 | 6/2012 | Moffitt |
| 2012/0165901 A1 | 6/2012 | Zhu et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0207378 A1 | 8/2012 | Gupta et al. |
| 2012/0226138 A1 | 9/2012 | DeSalles et al. |
| 2012/0229468 A1 | 9/2012 | Lee et al. |
| 2012/0239109 A1 | 9/2012 | Lee |
| 2012/0239115 A1 | 9/2012 | Lee |
| 2012/0265103 A1 | 10/2012 | Policker et al. |
| 2012/0265262 A1 | 10/2012 | Osorio |
| 2012/0265268 A1 | 10/2012 | Blum et al. |
| 2012/0271189 A1 | 10/2012 | Nelson et al. |
| 2012/0277833 A1 | 11/2012 | Gerber et al. |
| 2012/0302912 A1 | 11/2012 | Moffitt et al. |
| 2012/0303087 A1 | 11/2012 | Moffitt et al. |
| 2012/0303098 A1 | 11/2012 | Perryman |
| 2012/0314919 A1 | 12/2012 | Sparks et al. |
| 2012/0314924 A1 | 12/2012 | Carlton et al. |
| 2012/0316615 A1 | 12/2012 | Digiore et al. |
| 2012/0316619 A1 | 12/2012 | Goetz et al. |
| 2012/0330374 A1 | 12/2012 | Blum et al. |

(56) References Cited

U.S. PATENT DOCUMENTS

| | | |
|---|---|---|
| 2012/0330622 A1 | 12/2012 | Butson et al. |
| 2013/0035740 A1 | 2/2013 | Sharma et al. |
| 2013/0039550 A1 | 2/2013 | Blum et al. |
| 2013/0053926 A1 | 2/2013 | Hincapie Ordonez et al. |
| 2013/0060305 A1 | 3/2013 | Bokil |
| 2013/0105071 A1 | 5/2013 | Digiore et al. |
| 2013/0116744 A1 | 5/2013 | Blum et al. |
| 2013/0116748 A1 | 5/2013 | Bokil et al. |
| 2013/0116749 A1 | 5/2013 | Carlton et al. |
| 2013/0116929 A1 | 5/2013 | Carlton et al. |
| 2013/0150922 A1 | 6/2013 | Butson et al. |
| 2013/0197424 A1 | 8/2013 | Bedenbaugh |
| 2013/0197602 A1 | 8/2013 | Pianca et al. |
| 2013/0226261 A1 | 8/2013 | Sparks et al. |
| 2013/0245722 A1 | 9/2013 | Ternes et al. |
| 2013/0261684 A1 | 10/2013 | Howard |
| 2013/0289380 A1 | 10/2013 | Molnar et al. |
| 2013/0289660 A1 | 10/2013 | Molnar et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039586 A1 | 2/2014 | Barker et al. |
| 2014/0039587 A1 | 2/2014 | Romero |
| 2014/0063017 A1 | 3/2014 | Kaula et al. |
| 2014/0066999 A1 | 3/2014 | Carcieri et al. |
| 2014/0067018 A1 | 3/2014 | Carcieri et al. |
| 2014/0067022 A1 | 3/2014 | Carcieri et al. |
| 2014/0074180 A1 | 3/2014 | Heldman et al. |
| 2014/0081366 A1 | 3/2014 | Bentley et al. |
| 2014/0107731 A1 | 4/2014 | Stone et al. |
| 2014/0122379 A1 | 5/2014 | Moffitt et al. |
| 2014/0200633 A1 | 7/2014 | Moffitt |
| 2014/0243926 A1 | 8/2014 | Carcieri |
| 2014/0276707 A1 | 9/2014 | Jaax |
| 2014/0276927 A1 | 9/2014 | Barker |
| 2014/0277282 A1 | 9/2014 | Jaax |
| 2014/0277284 A1 | 9/2014 | Chen et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0073431 A1 | 3/2015 | Barker |
| 2015/0073432 A1 | 3/2015 | Barker |
| 2015/0134031 A1 | 5/2015 | Moffitt et al. |
| 2015/0151113 A1 | 6/2015 | Govea et al. |
| 2015/0246231 A1 | 9/2015 | Martens et al. |
| 2015/0360039 A1 | 12/2015 | Lempka et al. |
| 2016/0001087 A1 | 1/2016 | Moffitt |
| 2016/0008632 A1 | 1/2016 | Wetmore et al. |
| 2016/0022995 A1 | 1/2016 | Kothandaraman et al. |
| 2016/0023008 A1 | 1/2016 | Kothandaraman |
| 2016/0030749 A1 | 2/2016 | Carcieri et al. |
| 2016/0030750 A1 | 2/2016 | Bokil et al. |
| 2016/0045748 A1 | 2/2016 | Astrom et al. |
| 2016/0082252 A1 | 3/2016 | Hershey et al. |
| 2016/0096025 A1 | 4/2016 | Moffitt et al. |
| 2016/0136429 A1 | 5/2016 | Massoumi et al. |
| 2016/0136443 A1 | 5/2016 | Kothandaraman et al. |
| 2016/0144186 A1 | 5/2016 | Kaemmerer et al. |
| 2016/0175594 A1 | 6/2016 | Min et al. |
| 2016/0206380 A1 | 7/2016 | Sparks et al. |
| 2016/0228692 A1 | 8/2016 | Steinke et al. |
| 2016/0256691 A1 | 9/2016 | Cecchi et al. |
| 2016/0256693 A1 | 9/2016 | Parramon |
| 2016/0317800 A1 | 11/2016 | Barker |
| 2016/0346557 A1 | 12/2016 | Bokil |
| 2016/0375248 A1 | 12/2016 | Carcieri et al. |
| 2016/0375258 A1 | 12/2016 | Steinke |
| 2017/0100593 A1 | 4/2017 | Zottola |
| 2017/0100601 A1 | 4/2017 | Xiao et al. |
| 2017/0106197 A1 | 4/2017 | Wechter et al. |
| 2017/0197086 A1 | 7/2017 | Howard et al. |
| 2017/0225007 A1 | 8/2017 | Orinski |
| 2017/0252570 A1 | 9/2017 | Serrano Carmona et al. |
| 2017/0259078 A1 | 9/2017 | Howard |
| 2017/0304610 A1 | 10/2017 | Huibregtse et al. |
| 2017/0304633 A1 | 10/2017 | Zhang |
| 2017/0372039 A1 | 12/2017 | Mustakos et al. |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0104500 A1* | 4/2018 | Blum ................ A61N 1/36125 |
| 2018/0110971 A1 | 4/2018 | Serrano Carmona |
| 2018/0133481 A1 | 5/2018 | Von Zitzewitz et al. |
| 2018/0185650 A1 | 7/2018 | Shah |
| 2018/0193655 A1 | 7/2018 | Zhang et al. |
| 2018/0214700 A1 | 8/2018 | Vansickle et al. |
| 2018/0264278 A1 | 9/2018 | Laghi |
| 2018/0272142 A1 | 9/2018 | Zhang et al. |
| 2018/0280698 A1 | 10/2018 | Steinke et al. |
| 2018/0296828 A1 | 10/2018 | Bradley et al. |
| 2018/0333173 A1 | 11/2018 | Wang |
| 2018/0369589 A1* | 12/2018 | Schouenborg ..... A61N 1/36132 |
| 2018/0369606 A1 | 12/2018 | Zhang et al. |
| 2018/0369607 A1 | 12/2018 | Zhang et al. |
| 2019/0015660 A1 | 1/2019 | Zhang et al. |
| 2019/0105503 A1 | 4/2019 | Leven |
| 2019/0134403 A1* | 5/2019 | Steinke ............. A61N 1/37247 |
| 2019/0184167 A1* | 6/2019 | Vansickle .......... A61N 1/36185 |
| 2019/0184171 A1 | 6/2019 | Mustakos et al. |
| 2019/0209834 A1 | 7/2019 | Zhang et al. |
| 2019/0209849 A1 | 7/2019 | Hershey et al. |
| 2019/0262609 A1 | 8/2019 | Brill et al. |
| 2019/0275331 A1 | 9/2019 | Zhu |
| 2019/0329024 A1* | 10/2019 | Kothandaraman ......................... A61N 1/36171 |
| 2019/0329047 A1 | 10/2019 | Moffitt et al. |
| 2019/0329049 A1 | 10/2019 | Carcieri et al. |
| 2020/0094047 A1 | 3/2020 | Govea et al. |
| 2020/0139127 A1 | 5/2020 | Zhang et al. |
| 2020/0155854 A1 | 5/2020 | Leven et al. |
| 2020/0155859 A1 | 5/2020 | Blum et al. |
| 2020/0171298 A1 | 6/2020 | Goetz et al. |
| 2020/0171310 A1 | 6/2020 | Walter et al. |
| 2020/0179600 A1 | 6/2020 | Zanos et al. |
| 2020/0179688 A1* | 6/2020 | Su ........................ A61N 1/025 |
| 2020/0215330 A1 | 7/2020 | Huertas Fernandez et al. |
| 2020/0222704 A1 | 7/2020 | Moffitt et al. |
| 2020/0269053 A1 | 8/2020 | Park |
| 2020/0353254 A1 | 11/2020 | O Laighin et al. |
| 2020/0376262 A1 | 12/2020 | Clark et al. |
| 2020/0376263 A1 | 12/2020 | Zhu |
| 2020/0398057 A1 | 12/2020 | Esteller et al. |
| 2021/0008388 A1 | 1/2021 | Vansickle et al. |
| 2021/0008389 A1 | 1/2021 | Featherstone et al. |
| 2021/0016111 A1 | 1/2021 | Vansickle et al. |
| 2021/0023374 A1 | 1/2021 | Block et al. |
| 2021/0052893 A1 | 2/2021 | Suri et al. |
| 2021/0113844 A1 | 4/2021 | Zhang et al. |
| 2021/0128920 A1 | 5/2021 | Grill et al. |
| 2021/0196956 A1 | 7/2021 | Juárez Paz |
| 2021/0196964 A1* | 7/2021 | Schnell ................ A61B 5/372 |
| 2021/0205613 A1 | 7/2021 | Bradley et al. |
| 2021/0268268 A1 | 9/2021 | Horn et al. |
| 2021/0275820 A1 | 9/2021 | Grill, Jr. et al. |
| 2021/0387002 A1 | 12/2021 | Bourget et al. |
| 2022/0007980 A1 | 1/2022 | Single |
| 2022/0008729 A1 | 1/2022 | Zhu |
| 2022/0040485 A1 | 2/2022 | Li et al. |
| 2022/0062640 A1* | 3/2022 | Raike ................ A61N 1/36067 |
| 2022/0072329 A1 | 3/2022 | Howard |
| 2022/0111213 A1* | 4/2022 | Cassar ............... A61N 1/36132 |
| 2022/0126100 A1 | 4/2022 | Jackson et al. |
| 2022/0257950 A1 | 8/2022 | Moore et al. |

(56) References Cited

U.S. PATENT DOCUMENTS

| | | |
|---|---|---|
| 2022/0266026 A1 | 8/2022 | Case et al. |
| 2022/0296892 A1 | 9/2022 | Esteller et al. |
| 2022/0296893 A1 | 9/2022 | Steinke et al. |
| 2022/0339448 A1 | 10/2022 | Jayakumar et al. |
| 2022/0347479 A1 | 11/2022 | Esteller et al. |
| 2022/0355114 A1 | 11/2022 | Moore et al. |
| 2022/0355115 A1 | 11/2022 | Moore et al. |
| 2022/0370808 A1 | 11/2022 | Esteller |
| 2022/0387785 A1 | 12/2022 | Huynh et al. |
| 2022/0395690 A1 | 12/2022 | Haddock et al. |
| 2023/0048571 A1 | 2/2023 | Poltorak |
| 2023/0050186 A1* | 2/2023 | Rotenstreich ........ A61B 5/7267 |
| 2023/0064552 A1 | 3/2023 | Moffitt |
| 2023/0141183 A1 | 5/2023 | Moore et al. |
| 2023/0181089 A1 | 6/2023 | Zhang et al. |
| 2023/0181090 A1 | 6/2023 | Juarez Paz |
| 2023/0181906 A1 | 6/2023 | Moore et al. |
| 2023/0248977 A1 | 8/2023 | Esteller et al. |
| 2023/0264025 A1 | 8/2023 | Malekmohammadi et al. |
| 2023/0271015 A1 | 8/2023 | Malekmohammadi et al. |
| 2023/0277854 A1 | 9/2023 | Gaviao Kilmar |
| 2024/0065620 A1 | 2/2024 | Moore et al. |
| 2024/0157151 A1 | 5/2024 | Juarez Paz |
| 2024/0198110 A1 | 6/2024 | Moore |
| 2024/0316346 A1 | 9/2024 | Shah et al. |
| 2024/0359015 A1 | 10/2024 | Steinke et al. |
| 2025/0010079 A1 | 1/2025 | Bokil |
| 2025/0050107 A1 | 2/2025 | Moore et al. |

FOREIGN PATENT DOCUMENTS

| | | |
|---|---|---|
| EP | 1166819 | 1/2002 |
| EP | 1372780 | 1/2004 |
| EP | 1559369 | 8/2005 |
| WO | 97/39797 | 10/1997 |
| WO | 98/48880 | 11/1998 |
| WO | 01/90876 | 11/2001 |
| WO | 02/26314 | 4/2002 |
| WO | 02/28473 | 4/2002 |
| WO | 02/065896 | 8/2002 |
| WO | 02/072192 | 9/2002 |
| WO | 03/086185 | 10/2003 |
| WO | 2004/019799 A2 | 3/2004 |
| WO | 2004041080 | 5/2005 |
| WO | 2006017053 | 2/2006 |
| WO | 2006113305 | 10/2006 |
| WO | 20071097859 | 8/2007 |
| WO | 20071097861 A1 | 8/2007 |
| WO | 2007/100427 | 9/2007 |
| WO | 2007/100428 | 9/2007 |
| WO | 2007/112061 | 10/2007 |
| WO | 2009097224 | 8/2009 |
| WO | 2010/109448 | 9/2010 |
| WO | 2010/120823 A2 | 10/2010 |
| WO | 2011025865 | 3/2011 |
| WO | 2011/139779 A1 | 11/2011 |
| WO | 2011/159688 A2 | 12/2011 |
| WO | 2012088482 | 6/2012 |
| WO | 2016/025913 | 2/2016 |
| WO | 2016081099 | 5/2016 |
| WO | 2016112398 | 7/2016 |

OTHER PUBLICATIONS

""BioPSE" The Biomedical Problem Solving Environment", htt12://www.sci.utah.edu/cibc/software/index.html, MCRR Center for Integrative Biomedical Computing,(2004).

Andrews, R. J., "Neuroprotection trek-the next generation: neuromodulation I. Techniques—deep brain stimulation, vagus nerve stimulation, and transcranial magnetic stimulation.", Ann NY Acad Sci. 993. (May 2003),1-13.

Carnevale, N.T. et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

Chaturvedi, A. et al.: "Patient-specific models of deep brain stimulation: Influence of field model complexity on neural activation predictions." Brain Stimulation, Elsevier, Amsterdam, NL, vol. 3, No. Apr. 2, 2010, pp. 65-77.

Frankemolle, et al., "Reversing cognitive-motor impairments in Parkinson's disease patients using a computational modeling approach to deep brain stimulation programming," Brian 133 (2010), pp. 746-761.

McIntyre, C.C., et al., "Modeling the excitablitity of mammalian nerve fibers: influence of afterpotentials on the recovery cycle," J Neurophysiol, 87(2) (Feb. 2002), pp. 995-1006.

Peterson, et al., "Predicting myelinated axon activation using spatial characteristics of the extracellular field," Journal of Neural Engineering, 8 (2011), 12 pages.

Warman, et al., "Modeling the Effects of Electric Fields on nerver Fibers; Dermination of Excitation Thresholds," IEEE Transactions on Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. Jun. 2, 1998, pp. 200-207.

Andrews, R. J., "Neuroprotection trek-the next generation: neuromodulation II. Applications—epilepsy, nerve regeneration, neurotrophins.", Ann NY Acad Sci. 993 (May 2003), 14-24.

Astrom, M. , et al., "The effect of cystic cavities on deep brain stimulation in the basal ganglia: a simulation-based study", J Neural Eng., 3(2), (Jun. 2006).132-8.

Bazin et al., "Free Software Tools for Atlas-based Volumetric Neuroimage Analysis", Proc. SPIE 5747, Medical Imaging 2005: Image Processing, 1824 May 5, 2005.

Back, C. , et al., "Postoperative Monitoring of the Electrical Properties of Tissue and Electrodes in Deep Brain Stimulation", Neuromodulation, 6(4), (Oct. 2003 ),248-253.

Baker, K. B., et al., "Evaluation of specific absorption rate as a dosimeter of MRI-related implant heating", J Magn Reson Imaging., 20(2), (Aug. 2004),315-20.

Brown, J. "Motor Cortex Stimulation," Neurosurgical Focus ( Sep. 15, 2001) 11(3):E5.

Budai et al., "Endogenous Opioid Peptides Acting at m-Opioid Receptors in the Dorsal Horn Contribute to Midbrain Modulation of Spinal Nociceptive Neurons, " Journal of Neurophysiology (1998) 79(2): 677-687.

Cesselin, F. "Opioid and anti-opioid peptides," Fundamental and Clinical Pharmacology (1995) 9(5): 409-33 (Abstract only).

Rezai et al., "Deep Brain Stimulation for Chronic Pain" Surgical Management of Pain, Chapter 44 pp. 565-576 (2002).

Xu, MD., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.

Bedard, C. , et al., "Modeling extracellular field potentials and the frequency-filtering properties of extracellular space", Biophys J . . . 86(3). (Mar. 2004),1829-42.

Benabid, A. L., et al., "Future prospects of brain stimulation", Neurol Res.;22(3), (Apr. 2000),237-46.

Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977),440-443.

Butson, Christopher R., et al., "Deep Brain Stimulation of the Subthalamic Nucleus: Model-Based Analysis of the Effects of Electrode Capacitance on the vol. of Activation", Proceedings of the 2nd International IEEE EMBS, (Mar. 16-19, 2005),196-197.

Mcintyre, Cameron C., et al., "Cellular effects of deep brain stimulation: model-based analysis of activation and Inhibition," J Neurophysiol, 91(4) (Apr. 2004), pp. 1457-1469.

Chaturvedi, A., et al., "Subthalamic Nucleus Deep Brain Stimulation: Accurate Axonal Threshold Prediction with Diffusion Tensor Based Electric Field Models", Engineering in Medicine and Biol-

(56) References Cited

OTHER PUBLICATIONS ogy Society, 2006. EMBS' 06 28th Annual International Conference of the IEEE, IEEE, Piscataway, NJ USA, Aug. 30, 2006.

Butson, Christopher et al., "Predicting the Effects of Deep Brain Stimulation with Diffusion Tensor Based Electric Field Models" Jan. 1, 2001, Medical Image Computing and Computer-Assisted Intervention-Mic CAI 2006 Lecture Notes in Computer Science; LNCS, Springer, Berlin, DE.

Butson, C. R., et al., "Deep brainstimulation interactive visualization system", Society for Neuroscience vol. 898.7 (2005).

Hodaie, M., et al., "Chronic anterior thalamus stimulation for intractable epilepsy," Epilepsia, 43(6) (Jun. 2002), pp. 603-608.

Hoekema, R., et al., "Multigrid solution of the potential field in modeling electrical nerve stimulation," Comput Biomed Res., 31(5) (Oct. 1998), pp. 348-362.

Holsheimer, J., et al., "Identification of the target neuronal elements in electrical deep brain stimulation," Eur J Neurosci., 12(12) (Dec. 2000), pp. 4573-4577.

Jezernik, S., et al., "Neural network classification of nerve activity recorded in a mixed nerve," Neurol Res., 23(5) (Jul. 2001), pp. 429-434.

Jones, DK., et al., "Optimal strategies for measuring diffusion in anisotropic systems by magnetic resonance imaging," Magn. Reson. Med., 42(3) (Sep. 1999), pp. 515-525.

Krack, P., et al., "Postoperative management of subthalamic nucleus stimulation for Parkinson's disease," Mov. Disord., vol. 17(suppl 3) (2002), pp. 188-197.

Le Bihan, D., et al., "Diffusion tensor imaging: concepts and applications," J Magn Reson Imaging, 13(4) (Apr. 2001), pp. 534-546.

Lee, D. C., et al., "Extracellular electrical stimulation of central neurons: quantitative studies," In: Handbook of neuroprosthetic methods, WE Finn and PG Lopresti (eds) CRC Press (2003), pp. 95-125.

Levy, AL., et al., "An Internet-connected, patient-specific, deformable brain atlas integrated into a surgical navigation system," J Digit Imaging, 10(3 Suppl 1) (Aug. 1997), pp. 231-237.

Liu, Haiying, et al., "Intra-operative MR-guided DBS implantation for treating PD and ET," Proceedings of SPIE vol. 4319, Department of Radiology & Neurosurgery, University of Minnesota, Minneapolis, MN 55455 (2001), pp. 272-276.

Mcintyre, C. C., et al., "Extracellular stimulation of central neurons: influence of stimulus waveform and frequency on neuronal output," J. Neurophysiol., 88(4), (Oct. 2002), pp. 1592-1604.

Mcintyre, C. C., et al., "Microstimulation of spinal motoneurons: a model study," Proceedings of the 19th Annual International Conference of the IEEE Engineering in Medicine and Biology society, vol. 5, (1997), pp. 2032-2034.

Mcintyre, Cameron C., et al., "Model-based Analysis of deep brain stimulation of the thalamus," Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.

Mcintyre, C. C., et al., "Model-based design of stimulus trains for selective microstimulation of targeted neuronal populations," Proceedings of the 23rd Annual International Conference of the IEEE Engineering in Medicine and Biology Society, vol. 1 (2001), pp. 806-809.

Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc.] BM ES/EMBS Conference, vol. 1 (1999), p. 384.

Mcintyre, Cameron C., et al., "Selective microstimulation of central nervous system neurons," Annals of biomedical engineering, 28(3) (Mar. 2000), pp. 219-233.

Mcintyre, C. C., et al., "Sensitivity analysis of a model of mammalian neural membrane," Biol Cybern., 79(1) (Jul. 1998), pp. 29-37.

Mcintyre, Cameron C., et al., "Uncovering the mechanism(s) of action of deep brain stimulation: activation, inhibition, or both," Clin Neurophysiol, 115(6) (Jun. 2004), pp. 1239-1248.

Mcintyre, Cameron C., et al., "Uncovering the mechanisms of deep brain stimulation for Parkinson's disease through functional imaging, neural recording, and neural modeling," Crit Rev Biomed Eng., 30(4-6) (2002), pp. 249-281.

Mouine et al. "Multi-Strategy and Multi-Algorithm Cochlear Prostheses", Biomed. Sci. Instrument, 2000; 36:233-238.

Struijk, J J., et al., "Recruitment of dorsal column fibers in spinal cord stimulation: influence of collateral branching," IEEE Transactions on Biomedical Engineering, 39(9) (Sep. 1992), pp. 903-912.

Nakana, S., et al., "Fiber tract-based atlas of human white matter anatomy," Radiology, 230(1) (Jan. 2004), pp. 77-87.

Voghell et al., "Programmable Current Source Dedicated to Implantable Microstimulators" ICM '98 Proceedings of the Tenth International Conference, pp. 67-70.

Butson, Christopher R., et al., "Patient-specific analysis of the volume of tissue activated during deep brain stimulation", NeuroImage. vol. 34. (2007),661-670.

Alo, K. M., et al., "New trends in neuromodulation for the management of neuropathic pain," Neurosurgery, 50(4), (Apr. 2002), pp. 690-703, discussion pp. 703-704.

Ashby, P., et al., "Neurophysiological effects of stimulation through electrodes in the human subthalamic nucleus," Brain, 122 (PI 10), (Oct. 1999), pp. 1919-1931.

Baker, K. B., et al., "Subthalamic nucleus deep brain stimulus evoked potentials: Physiological and therapeutic implications," Movement Disorders, 17(5), (Sep./Ocl. 2002), pp. 969-983.

Bammer, R, et al., "Diffusion tensor imaging using single-shot SENSE-EPI", Magn Reson Med., 48(1 ), (Jul. 2002), pp. 128-136.

Basser, P J., et al., "MR diffusion tensor spectroscopy and imaging," Biophys J., 66(1 ), (Jan. 1994), pp. 259-267.

Basser, P J., et al., "New currents in electrical stimulation of excitable tissues," Annu Rev Biomed Eng., 2, (2000), pp. 377-397.

Benabid, AL., et al., "Chronic electrical stimulation of the ventralis intermedius nucleus of the thalamus as a treatment of movement disorders," J. Neurosurg., 84(2), (Feb. 1996), pp. 203-214.

Benabid, AL., et al., "Combined (Ihalamotoy and stimulation) stereotactic surgery of the VIM thalamic nucleus for bilateral Parkinson disease," Appl Neurophysiol, vol. 50, (1987), pp. 344-346.

Benabid, A L., et al., "Long-term suppression of tremor by chronic stimulation of the ventral intermediate thalamic nucleus," Lancet, 337 (8738), (Feb. 16, 1991 ), pp. 403-406.

Butson, C. R., et al., "Predicting the effects of deep brain stimulation with diffusion tensor based electric field models," Medical Image Computing and Computer-Assisted Intervention—Mic Cai 2006, Lecture Notes in Computer Science (LNCS), vol. 4191, pp. 429-437, LNCS, Springer, Berlin, DE.

Christensen, Gary E., et al., "Volumetric transformation of brain anatomy," IEEE Transactions on Medical Imaging, 16 (6), (Dec. 1997), pp. 864-877.

Cooper, S , et al., "Differential effects of thalamic stimulation parameters on tremor and paresthesias in essential tremor," Movement Disorders, 17(Supp. 5), (2002), p. S193.

Coubes, P, et al., "Treatment of DYT1-generalised dystonia by stimulation of the internal globus pallidus," Lancet, 355 (9222), (Jun. 24, 2000), pp. 2220-2221.

Dasilva, A.F. M., et al., "A Primer Diffusion Tensor Imaging of Anatomical Substructures," Neurosurg. Focus; 15(1) (Jul. 2003), pp. 1-4.

Dawant, B. M., et al., "Compuerized atlas-guided positioning of deep brain stimulators: a feasibility study," Biomedical Image registration, Second International Workshop, WBIR 2003, Revised Papers (Lecture notes in Comput. Sci. vol. (2717), Springer-Verlag Berlin, Germany(2003), pp. 142-150.

Finnis, K. W., et al., "3-D functional atalas of subcortical structures for image guided stereotactic neurosurgery," Neuroimage, vol. 9, No. 6, Iss. 2 (1999), p. S206.

Finnis, K. W., et al., "3D Functional Database of Subcorticol Structures for Surgical Guidance in Image Guided Stereotactic Neurosurgery," Medical Image Computing and Computer-Assisted

(56) References Cited

OTHER PUBLICATIONS

Intervention-MICCAI'99, Second International Conference. Cambridge, UK, Sep. 19-22, 1999, Proceedings (1999), pp. 758-767.
Finnis, K. W., et al., "A 3-Dimensional Database of Deep Brain Functional Anatomy, and Its Application to Image-Guided Neurosurgery," Proceedings of the Third International Conference on Medical Image Computing and Computer-Assisted Intervention. Lecture Notes In Computer Science; vol. 1935 (2000), pp. 1-8.
Finnis, K. W., et al., "A functional database for guidance of surgical and therapeutic procedures in the deep brain," Proceedings of the 22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention—Part 11, Lecture Notes In Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., "Stimulus waveforms for selective neural stimulation," IEEE Engineering in Medicine and Biology Magazine, 14(4) (Jul.-Aug. 1995), pp. 375-385.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Butson et al., "Tissue and Electrode Capacitance Reduce Neural Activation vols. During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 :S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 36:44-53, published online Sep. 2007.
Koop et al., "Improvement in a Quantitative Measure of Bradykinesia After Microelectrode Recording in Patients with Parkinson's Dis-

(56) References Cited

OTHER PUBLICATIONS ease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.
Machado et al., "Deep Brain Stimulation for Parkinson's Disease: Surgical Technique and Perioperative Management", Movement Disorders, 21 :S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638,Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
An, et al., "Prefronlal cortical projections to longitudinal columns in the midbrain periaqueductal gray in macaque monkeys," J Comp Neural 401 (4) (1998), pp. 455-479.
Carmichael, S. T., et al., "Connectional networks within the orbital and medial prefrontal cortex of macaque monkeys," J Comp Neural 371 (2) (1996), pp. 179-207.
Croxson, et al., "Quantitative investigation of connections of the prefrontal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: worldwide experience," Mol Psychiatry 15 (1) (2010), pp. 64-79.
Greenberg. et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834.
Hines, M. L., et al., "The NEURON simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L. et al., "Automated 3-Dimensional Brain Atlas Fitting to Microelectrode Recordings from Deep Brain Stimulation Surgeries," Stereotact. Fune!. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre, C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.
Nowinski, W. L., et al., "Statistical analysis of 168 bilateral subthalamic nucleus implantations by means of the probabilistic functional atlas.", Neurosurgery 57(4 Suppl) (Oct. 2005),319-30.
Obeso, J. A., et al., "Deep-brain stimulation of the subthalamic nucleus or the pars interna of the globus pallidus in Parkinson's disease.", N Engl J Med., 345{13I. The Deep-Brain Stimulation for Parkinson's Disease Study Group, (Sep. 27, 2001 ),956-63.
Butson et al.. "Current Steering to control the volume of tissue activated during deep brain stimulation," vol. 1, No. 1, Dec. 3, 2007, pp. 7-15.
Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001),31-41.
Phillips, M. D., et al., "Parkinson disease: pattern of functional MR imaging activation during deep brain stimulation of subthalamic nucleus—initial experience", Radiology 239(1). (Apr. 2006), 209-16.

(56) References Cited

OTHER PUBLICATIONS

Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.
Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.
Olivier Commowick et al., "Using Frankenstein's Creature Paradigm to Build a Patient Specific Atlas," Sep. 20, 2009, Medical Image Computing and Computer-Assisted Intervention, pp. 993-1000.
Lotjonen J.M.P. et al., "Fast and robust multi-atlas segmentation of brain magnetic resonance images," NeuroImage, Academic Press, vol. 49, No. 3, Feb. 1, 2010, pp. 2352-2365.
McIntyre, C. C., et al., "How does deep brain stimulation work? Present understanding and future questions.", J Clin Neurophysiol. 21 (1 ). (Jan.-Feb. 2004 ), 40-50.
Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.
Plaha, P. , et al., "Stimulation of the caudal zona incerta is superior to stimulation of the subthalamic nucleus in Improving contralateral parkinsonism.", Brain 129{Pt 7) (Jul. 2006), 1732-4 7.
Rattay, F, "Analysis of models for external stimulation of axons", IEEE Trans. Biomed. Eng. vol. 33 (1986), 974-977.
Rattay, F., "Analysis of the electrical excitation of CNS neurons", IEEE Transactions on Biomedical Engineering 45 (6). (Jun. 1998), 766-772.
Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.
Rubinstein, J. T., et al., "Signal coding in cochlear implants: exploiting stochastic effects of electrical stimulation", Ann Otol Rhinol Laryngol Suppl . . . 191, (Sep. 2003), 14-9.
Schwan, H.P., et al., "The conductivity of living tissues.", Ann NY Acad Sci., 65(6). (Auq., 1957), 1007-13.
Taylor, R. S., et al., "Spinal cord stimulation for chronic back and leg pain and failed back surgery syndrome: a systematic review and analysis of prognostic factors", Spine 30(1 ). (Jan. 1, 2005), 152-60.
Siegel, Ralph M. et al., "Spatiotemporal dynamics of the functional architecture for gain fields in inferior parietal obule of behaving monkey," Cerebral Cortex, New York, NY, vol. 17, No. 2, Feb. 2007, pp. 378-390.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Geddes, L. A., et al., "The specific resistance of biological material-a compendium of data for the biomedical engineer and physiologist.", Med Biol Ena. 5(3). (May 1967),271-93.
Gimsa, J., et al., "Choosing electrodes for deep brain stimulation experiments-electrochemical considerations.", J Neurosci Methods, 142(2), (Mar. 30, 2005),251-65.
Vidailhet, M. , et al., "Bilateral deep-brain stimulation of the globus pallidus in primary generalized dystonia", N Engl J Med. 352(5) (Feb. 3, 2005),459-67.
Izad, Oliver, "Computationally Efficient Method in Predicating Axonal Excitation," Dissertation for Master Degree, Department of Biomedical Engineering, Case Western Reserve University, May 2009.
Jaccard, Paul, "Elude comparative de la distribution florale dans une portion odes Aples et des Jura," Bulletin de la Societe Vaudoise des Sciences Naturelles (1901), 37:547-579.

Dice, Lee R., "Measures of the Amount of Ecologic Association Between Species," Ecology 26(3) (1945): 297-302. doi: 10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi:10.1007/ BF01908075.
Cover, T.M. et al., "Elements of information theory," (1991) John Wiley & Sons, New York, NY.
Meila, Marina, "Comparing Clusterings by the Variation of Information," Learning Theory and Kernel Machines (2003): 173-187.
Viola, P., et al., "Alignment by maximization of mutual information", International Journal of Com outer Vision 24(2). (1997), 137-154.
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the vol. of Tissue Activated During Deep Brain Stimulation," Journal of Neural Engineering, Mar. 1, 2006, vol. 3, No. 1, pp. 1-8.
Volkmann et al., Indroduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al. "Sketching and Composing Widgets for 3D Manipulation," Eurographics, Apr. 2008, vol. 27, No. 2, pp. 301-310.
Volkmann, J. , et al., "Basic algorithms for the programming of deep brain stimulation in Parkinson's disease", Mov Disord., 21 Suppl 14. (Jun. 2006),S284-9.
Walter, B. L., et al., "Surgical treatment for Parkinson's disease", Lancet Neural. 3(12). (Dec. 2004),719-28.
Wei, X. F., et al., "Current density distributions, field distributions and impedance analysis of segmented deep brain stimulation electrodes", J Neural Eng . . . 2(4). (Dec. 2005), 139-47.
Zonenshayn, M. , et al., "Location of the active contact within the subthalamic nucleus (STN) in the treatment of diopathic Parkinson's disease.", Surg Neurol., 62(3) (Sep. 2004), 216-25.
Da Silva et al (A primer on diffusion tensor imaging of anatomical substructures. Neurosurg Focus 15(1): p. 1-4, Article 4, 2003.).
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4), (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J. , et al., "Electron microscopy of tissue adherent to explanted electrodes in dystonia and Parkinson's disease", Brain, 127{Pt 12). (Dec., 2004 ),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.
McIntyre, Cameron , et al., "Finite element analysis of the current-density and electric field generated by metal microelectrodes", Ann Biomed Eng . 29(3), (2001 ),227-235.

(56) References Cited

OTHER PUBLICATIONS

Foster, K. R., et al., "Dielectric properties of tissues and biological materials: a critical review.", Grit Rev Biomed Ena. 17(1 ). {1989),25-104.
Limousin, P., et al., "Electrical stimulation of the subthalamic nucleus in advanced Parkinson's disease", N Engl J Med . . . 339(16), (Oct. 15, 1998), 1105-11.
Kitagawa, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1). (Apr. 1, 2000),45-50.
Hines, M. L., et al., "The NEURON simulation environment", Neural Comput. 9(6). (Aug. 15, 1997), 1179-209.
Herzog, J., et al., "Most effective stimulation site in subthalamic deep brain stimulation for Parkinson's disease", Mov Disord. 19(9). (Sep. 2004),1050-4.
Hershey, T., et al., "Cortical and subcortical blood flow effects of subthalamic nucleus stimulation in PD.", Neurology 61(6). (Sep. 23, 2003),816-21.
Hemm, S. , et al., "Evolution of Brain Impedance in Dystonic Patients Treated by GPi Electrical Stimulation", Neuromodulation 7(2) (Apr. 2004),67-75.
Jemm, S., et al., "Deep brain stimulation in movement disorders: stereotactic coregistration of two-dimensional electrical field modeling and magnetic resonance imaging.", J Neurosurg. 103(6): (Dec. 2005),949-55.
Haueisen, J, et al., "The influence of brain tissue anisotropy on human EEG and MEG", Neuroimage 15(1) (Jan. 2002),159-166.
Haslinger, B., et al., "Frequency-correlated decreases of motor cortex activity associated with subthalamic nucleus stimulation in Parkinson's disease.", Neuroimage 28(3). (Nov. 15, 2005),598-606.
Hashimoto, T. , et al., "Stimulation of the subthalamic nucleus changes the firing pattern of pallidal neurons", J Neurosci. 23(5). (Mar. 1, 2003),1916-23.
Hardman, C. D., et al., "Comparison of the basal ganglia in rats, marmosets, macaques, baboons, and humans: vol. and neuronal number for the output, internal relay, and striatal modulating nuclei", J Comp Neurol., 445(3). (Apr. 8, 2002),238-55.
McNaughtan et al., "Electrochemical Issues in Impedance Tomography", 1st World Congress on Industrial Process Tomography, Buxton, Greater Manchester, Apr. 14-17, 1999.
Grill, WM., et al., "Electrical properties of implant encapsulation tissue", Ann Biomed Eng. vol. 22. (1994),23-33.
Grill, W. M., et al., "Deep brain stimulation creates an informational lesion of the stimulated nucleus", Neuroreport. 15I7t (May 19, 2004 ), 1137-40.
International Search Report and Written Opinion for PCT Application No. PCT/US2022/026162 mailed Jul. 25, 2022.
Pulliam CL, Heldman DA, Orcutt TH, Mera TO, Giuffrida JP, Vitek JL. Motion sensor strategies for automated optimization of deep brain stimulation in Parkinson's disease. Parkinsonism Relat Disord. Apr. 2015;21(4):378-82.
Benoit M. Dawant et al: "The VU-DBS project: integrated and computer-assisted planning, intra-operative placement, and post-operative programming of deep-brain stimulators", Proceedings of SPIE, vol. 6509, Mar. 6, 2007 (Mar. 6, 2007), 11 pages.
Mitra PP, Pesaran B. Analysis of dynamic brain imaging data. Biophys J. Feb. 1999; 76(2):691-708. doi: 10.1016/S0006-3495(99)77236-X. PMID: 9929474; PMCID: PMC1300074.
Hammer N, Glätzner J, Feja C, Kühne C, Meixensberger J, et al. (2015) Human Vagus Nerve Branching in the Cervical Region. Plos One 10(2): e0118006. Published: Feb. 13, 2015. https://doi.org/10.1371/journal.pone.0118006.

Trost M, Su S, Su P, Yen RF, Tseng HM, Barnes A, Ma Y, Eidelberg D. Network modulation by the subthalamic nucleus in the treatment of Parkinson's disease. Neuroimage. May 15, 2006;31(1):301-7. doi: 10.1016/j.neuroimage.2005.12.024. Epub Feb. 8, 2006.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
Micheli-Tzanakou, E. , et al., "Computational Intelligence for target assesment in Parkinson's disease," Proceedings of SPIE vol. 4479, Applications and Science of Neural Networks, Fuzzy Systems, and Evolutionary Computation IV (2001 ), pp. 54-69.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Enginering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E, et al., "The impact on Parkinson's disease of electrical parameter settings in STN stimulation," Neurology, 59 (5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems," Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.

(56) References Cited

OTHER PUBLICATIONS

Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.

Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.

Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.

Sances, A., et al., "In Electroanesthesia: Biomedical and Biophysical Studies," A Sances and SJ Larson, Eds., Academic Press, NY (1975), pp. 114-124.

Sl. Jean, P., et al., "Automated atlas integration and interactive three-dimensional visualization tools for planning and guidance in functional neurosurgery," IEEE Transactions on Medical Imaging, 17(5) (1998), pp. 672-680.

Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.

Sterio, D., et al., "Neurophysiological refinement of subthalamic nucleus targeting," Neurosurgery, 50(1) (Jan. 2002), pp. 58-69.

Struijk, J. J., et al., "Excitation of dorsal root fibers in spinal cord stimulation: a theoretical study," IEEE Transactions on Biomedical Engineering, 40(7) (Jul. 1993), pp. 632-639.

Struijk, J J., et al., "Recruitment of dorsal col. fibers in spinal cord stimulation: influence of collateral branching," IEEE Transactions on Biomedical Engineering, 39(9) (Sep. 1992), pp. 903-912.

Tamma, F., et al., "Anatomo-clinical correlation of intraoperative stimulation-induced side effects during HF-DBS of the subthalamic nucleus," Neurol Sci., vol. 23 (Suppl 2) (2002), pp. 109-110.

Tarler, M., et al., "Comparison between monopolar and tripolar configurations in chronically implanted nerve cuff electrodes," IEEE 17th Annual Conference Engineering in Medicine and Biology Society, vol. 2 (1995), pp. 1093-1109.

Testerman, Roy L., "Coritical response to callosal stimulation: A model for determining safe and efficient stimulus parameters," Annals of Biomedical Engineering, 6(4) (1978), pp. 438-452.

Tuch, D.S., et al., "Conductivity mapping of biological tissue using diffusion MRI," Ann NY Acad Sci., 888 (Oct. 30, 1999), pp. 314-316.

Tuch, D.S., et al., "Conductivity tensor mapping of the human brain using diffusion tensor MRI," Proc Nall Acad Sci USA, 98(20) (Sep. 25, 2001), pp. 11697-11701.

Veraart, C., et al., "Selective control of muscle activation with a multipolar nerve cuff electrode," IEEE Transactions on Biomedical Engineering, 40(7) (Jul. 1993), pp. 640-653.

Vercueil, L., et al., "Deep brain stimulation in the treatment of severe dystonia," J. Neurol., 248(8) (Aug. 2001 ), pp. 695-700.

Vilalte, "Circuit Design of the Power-on-Reset," Apr. 2000, pp. 1-25.

Vitek, J. L., "Mechanisms of deep brain stimulation: excitation or inhibition," Mov. Disord., vol. 17 (Suppl. 3) (2002), pp. 69-72.

Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.

Wakana, S., et al., "Fiber tract-based atlas of human white matter anatomy," Radiology, 230(1) (Jan. 2004), pp. 77-87.

Alexander, DC., et al., "Spatial transformations of diffusion tensor magnetic resonance images," IEEE Transactions on Medical Imaging, 20 (11), (2001), pp. 1131-1139.

Wu, Y. R., et al., "Does Stimulation of the GPi control dyskinesia by activating inhibitory axons?," Mov. Disord., vol. 16 (2001), pp. 208-216.

Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.

Yianni, John, et al., "Globus pallidus internus deep brain stimulation for dystonic conditions: a prospective audit," Mov. Disord., vol. 18 (2003), pp. 436-442.

Zonenshayn, M., et al., "Comparison of anatomic and neurophysiological methods for subthalamic nucleus targeting," Neurosurgery, 47(2) (Aug. 2000), pp. 282-294.

Voghell et al., "Programmable Current Source Dedicated to Implantable Microstimulators" ICM '98 Proceedings of the Tenth International Conference, pp. 67-70, (Dec. 1998).

Butson, Christopher R., et al., "Patient-specific analysis of the volume of tissue activated during deep brain stimulation", NeuroImage. vol. 34. (2007),661-670.

Adler, DE., et al., "The tentorial notch: anatomical variation, morphometric analysis, and classification in 100 human autopsy cases," J. Neurosurg., 96(6), (Jun. 2002), pp. 1103-1112.

Jones et al., "An Advanced Demultiplexing System for Physiological Stimulation", IEEE Transactions on Biomedical Engineering, vol. 44 No. Dec. 12, 1997, pp. 1210-1220.

\* cited by examiner

SYSTEMS AND METHODS FOR AUTOMATED PROGRAMMING OF ELECTRICAL STIMULATION

CROSS-REFERENCE TO RELATED APPLICATIONS

This application claims the benefit under 35 U.S.C. § 119(e) of U.S. Provisional Patent Application Ser. No. 63/180,380, filed Apr. 27, 2021, which is incorporated herein by reference.

FIELD

The present disclosure is directed to the area of methods and systems for at least partially automating programming of electrical stimulation. The present disclosure is also directed to methods and systems for automating the testing of multiple sets of electrical stimulation parameters.

BACKGROUND

Implantable electrical stimulation systems have proven therapeutic in a variety of diseases and disorders. For example, deep brain stimulation systems have been used as a therapeutic modality for the treatment of Parkinson's disease, essential tremor, and the like.

Stimulators have been developed to provide therapy for a variety of treatments. A stimulator can include an implantable pulse generator (IPG), one or more leads, and an array of stimulator electrodes on each lead. The stimulator electrodes are in contact with or near the nerves, muscles, or other tissue to be stimulated. The pulse generator in the IPG generates electrical pulses that are delivered by the electrodes to body tissue.

Implantable medical devices (IMDs), including IPGs, typically have the capability to communicate data with an external device, such as a clinician programmer or a remote control, via a radio-frequency telemetry link or other wireless communication method. The clinician programmer can program the operating parameters of the implanted medical device. The remote control can switch programs. Modern implantable devices also include the capability for bidirectional communication so that information can be transmitted to the clinician programmer or remote control from the implanted device.

BRIEF SUMMARY

One aspect is a method for automating selection of stimulation parameters for a stimulation device implanted in a patient. The method includes setting, by a user, at least one limit on each of at least one stimulation parameter and performing, automatically using at least one processor, the following actions for each of a plurality of sets of the stimulation parameters constrained by the at least one limit: stimulating the patient, by the stimulation device, using the set of stimulation parameters, sensing one or more effects arising in response to the stimulation, and updating, by the at least one processor, a collection of the effects and sets of stimulation parameters with the one or more effects and the set of stimulation parameters. The method further includes selecting, by the processor, one of the sets of stimulation parameters based on the effects.

In at least some aspects, the method further includes, after selecting the one of the sets of stimulation parameters, fine-tuning, manually by the user, the stimulation parameters of the one of the sets of stimulation parameters. In at least some aspects, the method further includes programming the stimulation device with the one of the sets of stimulation parameters.

In at least some aspects, the sensing includes sensing a signal from the stimulated tissue. In at least some aspects, the signal is an evoked compound action potential (ECAP), evoked resonant neural activity (ERNA), or local field potential (LFP). In at least some aspects, at least one of the one or more effects is a feature of the signal, wherein the feature is a range of the signal, an area under a curve of the signal, a length of the curve of the signal, a maximum of the signal, or a minimum of the signal.

In at least some aspects, the performing includes performing the actions for sets of stimulation parameters at different axial locations along an electrical stimulation lead and selecting a one of the different axial locations based on the sensed one or more effects. In at least some aspects, the performing further includes, after selecting the one of the different axial locations, performing the actions for sets of stimulation parameters at second axial locations within one axial electrode spacing of the selected one of the different axial locations and selecting one of the second axial locations or the selected one of the different axial locations. In at least some aspects, the performing further includes, after selecting the one of the different axial locations, performing the actions for sets of stimulation parameters at different rotational directions around the electrical stimulation lead at the selected one of the different axial locations and selecting a one of the different rotational directions based on the sensed one or more effects. In at least some aspects, the performing further includes, after selecting the one of the different rotational directions, performing the actions for sets of stimulation parameters at second rotational directions within 120 degrees of the selected one of the different rotational directions and selecting one of the second rotational directions or the selected one of the different rotational directions. In at least some aspects, the performing further includes, after selecting the one of the different rotational directions, performing the actions for sets of stimulation parameters at different stimulation amplitudes for the selected one of the different rotational directions and selecting one of the stimulation amplitudes.

Another aspect is a system for selection of stimulation parameters for a stimulation device implanted in a patient. The system includes at least one processor configured to perform actions, the actions including receiving, from a user, at least one limit for each of at least one stimulation parameter and performing the following actions for each of a plurality of sets of the stimulation parameters constrained by the at least one limit: directing the stimulation device to stimulate the patient using the set of stimulation parameters, sensing one or more effects arising in response to the stimulation, and updating a collection of the effects and sets of stimulation parameters with the one or more effects and the set of stimulation parameters. The actions further include selecting one of the sets of stimulation parameters based on the effects.

In at least some aspects, the system further includes the stimulation device. In at least some aspects, the stimulation device includes an electrical stimulation lead having electrodes disposed along a distal portion of the electrical stimulation lead. In at least some aspects, sensing one or more effects including sensing the one or more effects arising in response to the stimulation using at least one of the electrodes of the electrical stimulation lead. In at least some aspects, the system further includes a sensor external to the stimulation device, wherein sensing one or more effects including sensing the one or more effects arising in response to the stimulation using the sensor. In at least some aspects, the actions further include programming the stimulation device with the one of the sets of stimulation parameters.

Yet another aspect is a non-transitory computer-readable medium having stored thereon instructions for execution by at least one processor. The instructions include receiving, from a user, at least one limit for each of at least one stimulation parameter and performing the following actions for each of a plurality of sets of the stimulation parameters constrained by the at least one limit: directing the stimulation device to stimulate the patient using the set of stimulation parameters, sensing one or more effects arising in response to the stimulation, and updating a collection of the effects and sets of stimulation parameters with the one or more effects and the set of stimulation parameters. The instructions further including selecting one of the sets of stimulation parameters based on the effects.

In at least some aspects, the instructions further include, after selecting the one of the sets of stimulation parameters, fine-tuning, manually by the user, the stimulation parameters of the one of the sets of stimulation parameters. In at least some aspects, the instructions further include programming the stimulation device with the one of the sets of stimulation parameters. In at least some aspects, the instructions further include repeating the performing instruction periodically to track disease progression over time

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of methods and systems for at least partially automating programming of electrical stimulation. The present disclosure is also directed to methods and systems for automating the testing of multiple sets of electrical stimulation parameters.

Implantable electrical stimulation systems and devices are used herein to exemplify the inventions, but it will be understood that these inventions can be utilized with other stimulation systems and devices. Examples of implantable electrical stimulation systems include, but are not limited to, a least one lead with one or more electrodes disposed along a distal end of the lead and one or more terminals disposed along the one or more proximal ends of the lead. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 8,175,710; 8,224,450; 8,271,094; 8,295,944; 8,364,278; and 8,391,985; U.S. Patent Application Publications Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 1:
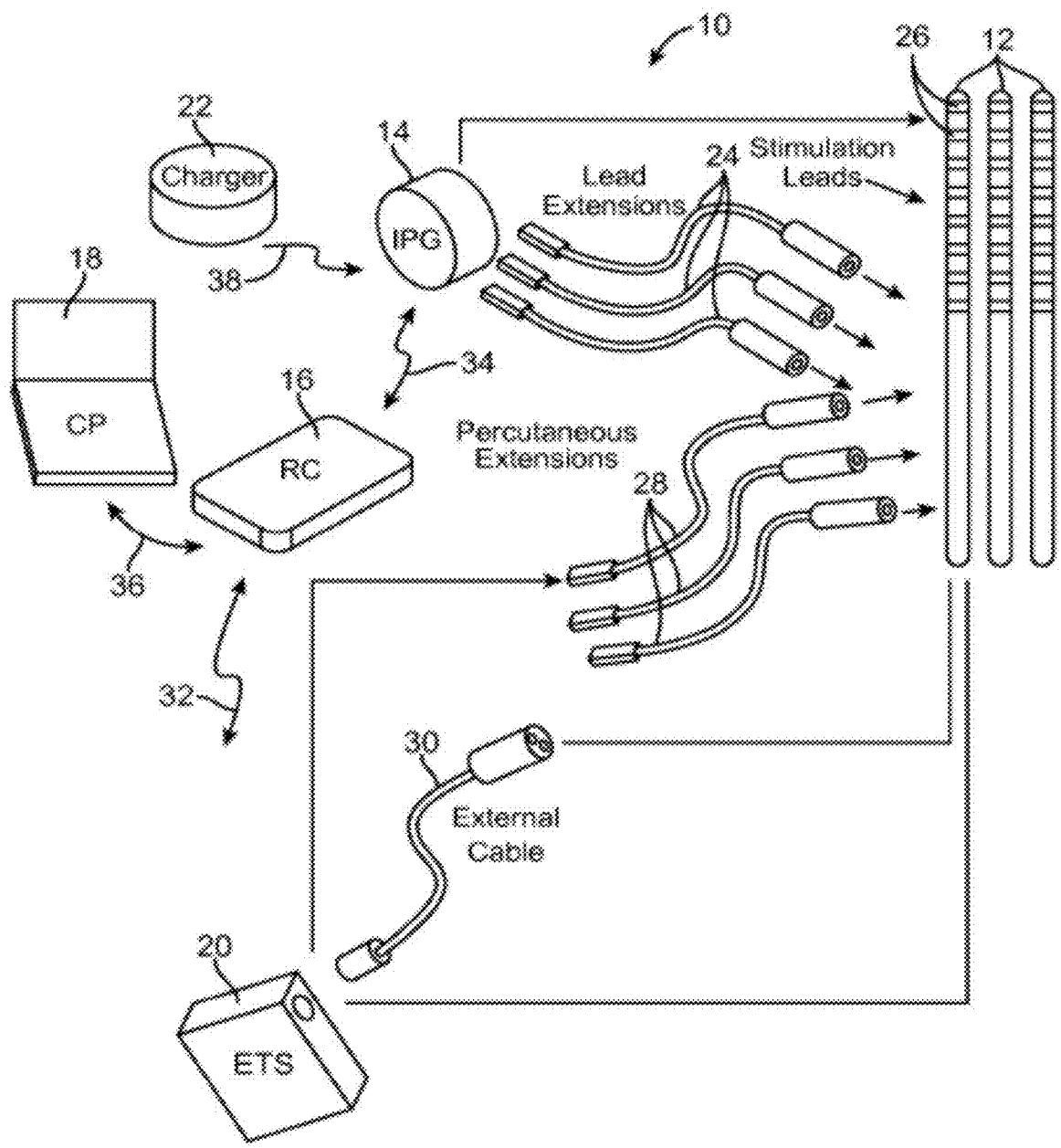
FIG. 1 is a schematic view of one embodiment of an electrical stimulation system that includes one or more leads that can be coupled to an IPG.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's abdominal cavity or at any other suitable site. The implantable pulse generator 14 can have multiple stimulation channels which may be independently programmable to control the magnitude of the current stimulus from each channel. In some embodiments, the implantable pulse generator 14 can have any suitable number of stimulation channels including, but not limited to, 4, 6, 8, 12, 16, 32, or more stimulation channels. The implantable pulse generator 14 can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14, for example, to be turned on or off and to be programmed with different stimulation parameter sets. The IPG 14 may also be operated to modify the programmed stimulation parameters to actively control the characteristics of the electrical stimulation energy output by the IPG 14. In at least some embodiments, the CP 18 (or RC 16 or other programming device) allows a user, such as a clinician, the ability to program stimulation parameters for the IPG 14 and ETS 20 in the operating room and in follow-up sessions. Alternately, or additionally, in at least some embodiments, stimulation parameters can be programed via wireless communications (e.g., Bluetooth) between the RC 16 (or other external device such as a hand-held electronic device like a mobile phone, tablet, or the like) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). In at least some embodiments, the stimulation parameters provided by the CP 18 are also used to program the RC 16, so that the stimulation parameters can be subsequently modified by operation of the RC 16 in a stand-alone mode (i.e., without the assistance of the CP 18). The CP 18 or RC 16 can be any suitable device including, but not limited to, a computer or other computing device, laptop, mobile device (for example, a mobile phone or tablet), or the like or any combination thereof. The CP 18 or RC 16 can include software applications for interacting with the IPG 14 or ETS 20 and for programming the IPG 14 or ETS 20.

Additional examples of the RC 16, CP 18, ETS 20, and external charger 22 can be found in the references cited herein as well as U.S. Pat. Nos. 6,895,280; 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, all of which are incorporated herein by reference in their entireties.

Figure 2:
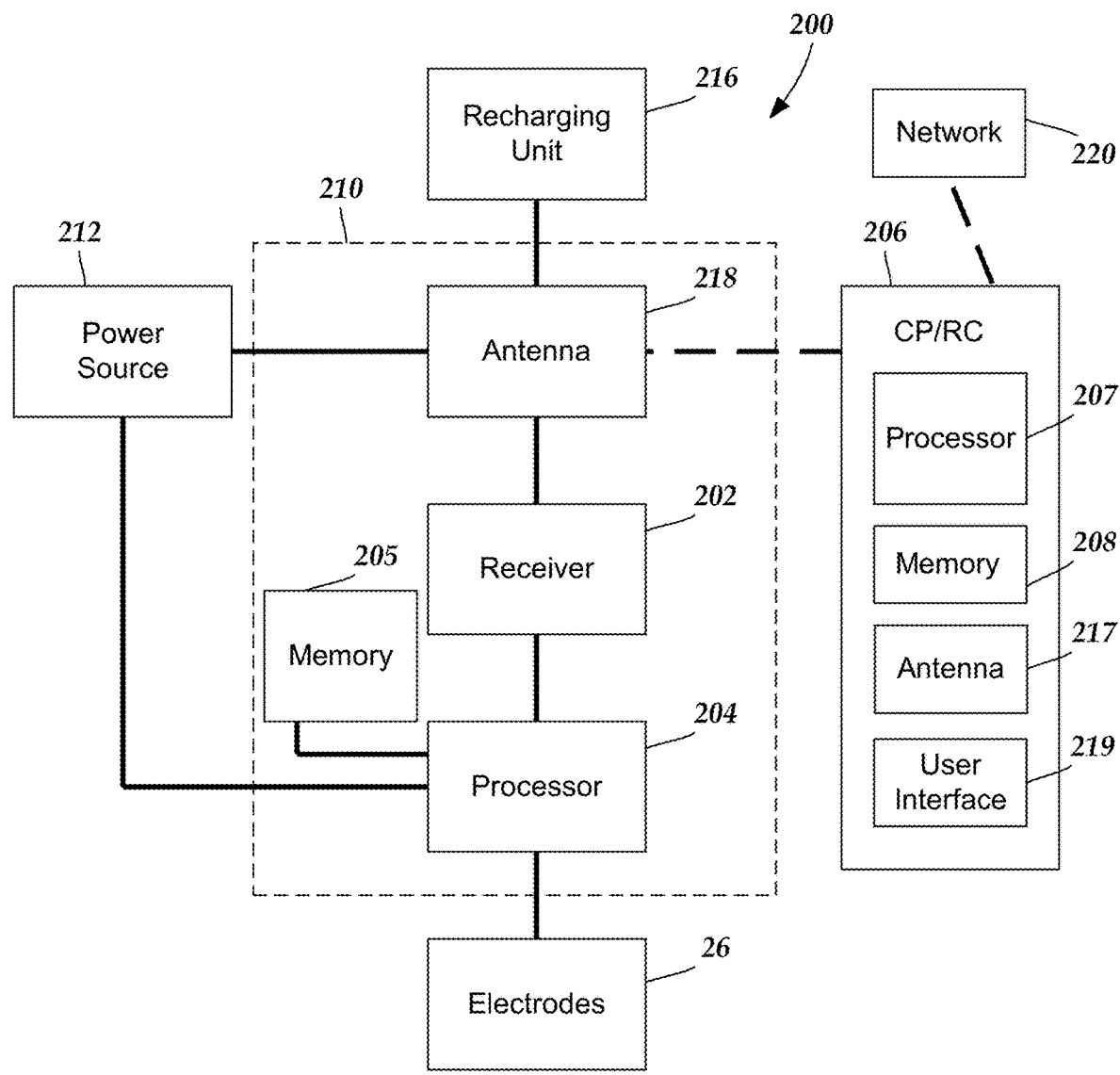
FIG. 2 is a block diagram of elements of an electrical stimulation system.

FIG. 2 is a schematic overview of one embodiment of components of an electrical stimulation system 200 including an electronic subassembly 210 disposed within an IPG 14 (FIG. 1). It will be understood that the electrical stimulation system can include more, fewer, or different components and can have a variety of different configurations including those configurations disclosed in the stimulator references cited herein.

The IPG 14 (FIG. 1) can include, for example, a power source 212, antenna 218, receiver 202, processor 204, and memory 205. Some of the components (for example, power source 212, antenna 218, receiver 202, processor 204, and memory 205) of the electrical stimulation system can be positioned on one or more circuit boards or similar carriers within a sealed housing of the IPG 14 (FIG. 1), if desired. Unless indicated otherwise, the term "processor" refers to both embodiments with a single processor and embodiments with multiple processors.

An external device, such as a CP or RC 206, can include a processor 207, memory 208, an antenna 217, and a user interface 219. The user interface 219 can include, but is not limited to, a display screen on which a digital user interface can be displayed and any suitable user input device, such as a keyboard, touchscreen, mouse, track ball, or the like or any combination thereof.

Any power source 212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the antenna 218 or a secondary antenna. The external power source can be in a device that is mounted on the skin of the user or in a unit that is provided near the user on a permanent or periodic basis.

If the power source 212 is a rechargeable battery, the battery may be recharged using the antenna 218, if desired. Power can be provided to the battery for recharging by inductively coupling the battery through the antenna to a recharging unit 216 external to the user. Examples of such arrangements can be found in the references identified above.

In one embodiment, electrical current is emitted by the electrodes 26 on the lead body to stimulate nerve fibers, muscle fibers, or other body tissues near the electrical stimulation system. A processor 204 is generally included to control the timing and electrical characteristics of the electrical stimulation system. For example, the processor 204 can, if desired, control one or more of the timing, frequency, amplitude, width, and waveform of the pulses. In addition, the processor 204 can select which electrodes can be used to provide stimulation, if desired. In some embodiments, the processor 204 may select which electrode(s) are cathodes and which electrode(s) are anodes. In some embodiments, the processor 204 may be used to identify which electrodes provide the most useful stimulation of the desired tissue. Instructions for the processor 204 can be stored on the memory 205. Instructions for the processor 207 can be stored on the memory 208.

Any processor 204 can be used for the IPG and can be as simple as an electronic device that, for example, produces pulses at a regular interval or the processor can be capable of receiving and interpreting instructions from the CP/RC 206 (such as CP 18 or RC 16 of FIG. 1) that, for example, allows modification of pulse characteristics. In the illustrated embodiment, the processor 204 is coupled to a receiver 202 which, in turn, is coupled to the antenna 218. This allows the processor 204 to receive instructions from an external source to, for example, direct the pulse characteristics and the selection of electrodes, if desired. Any suitable processor 207 can be used for the CP/RC 206.

Any suitable memory 205, 208 can be used including computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include, but are not limited to, RAM, ROM, EEPROM, flash memory, or other memory technology/#CD-ROM, digital versatile disks ("DVD") or other optical storage, magnetic cassettes, magnetic tape, magnetic disk storage or other magnetic storage devices, or any other medium which can be used to store the desired information and which can be accessed by a processor.

In one embodiment, the antenna 218 is capable of receiving signals (e.g., RF signals) from an antenna 217 of a CP/RC 206 (see, CP 18 or RC 16 of FIG. 1) which is programmed or otherwise operated by a user. The signals sent to the processor 204 via the antenna 218 and receiver 202 can be used to modify or otherwise direct the operation of the electrical stimulation system. For example, the signals may be used to modify the pulses of the electrical stimulation system such as modifying one or more of pulse width, pulse frequency, pulse waveform, and pulse amplitude. The signals may also direct the electrical stimulation system 200 to cease operation, to start operation, to start signal acquisition, to stop signal acquisition, to start charging the battery, or to stop charging the battery. In other embodiments, the stimulation system does not include an antenna 218 or receiver 202 and the processor 204 operates as programmed.

Optionally, the electrical stimulation system 200 may include a transmitter (not shown) coupled to the processor 204 and the antenna 218 for transmitting signals back to the CP/RC 206 or another unit capable of receiving the signals. For example, the electrical stimulation system 200 may transmit signals indicating whether the electrical stimulation system 200 is operating properly or not or indicating when the battery needs to be charged or the level of charge remaining in the battery. The processor 204 may also be capable of transmitting information about the pulse characteristics so that a user or clinician can determine or verify the characteristics.

Transmission of signals can occur using any suitable method, technique, or platform including, but not limited to, inductive transmission, radiofrequency transmission, Bluetooth™, Wi-Fi, cellular transmission, near field transmission, infrared transmission, or the like or any combination thereof. In addition, the IPG 14 can be wirelessly coupled to the RC 16 or CP 18 using any suitable arrangement include direct transmission or transmission through a network, such as a local area network, wide area network, the Internet, or the like or any combination thereof. The CP 18 or RC 16 may also be capable of coupling to, and sending data or other information to, a network 220, such as a local area network, wide area network, the Internet, or the like or any combination thereof.

At least some of the stimulation electrodes can take the form of segmented electrodes that extend only partially around the perimeter (for example, the circumference) of the lead. These segmented electrodes can be provided in sets of electrodes, with each set having electrodes circumferentially distributed about the lead at a particular longitudinal position.

Figure 3A:
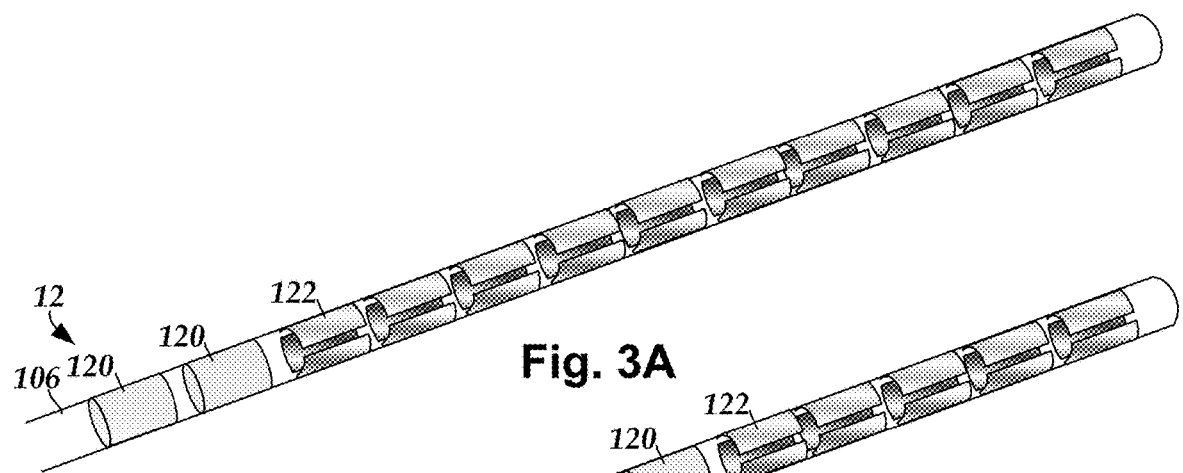
FIG. 3A is a schematic perspective view of a distal portion of one embodiment of an electrical stimulation lead with segmented electrodes.
Figure 3B:
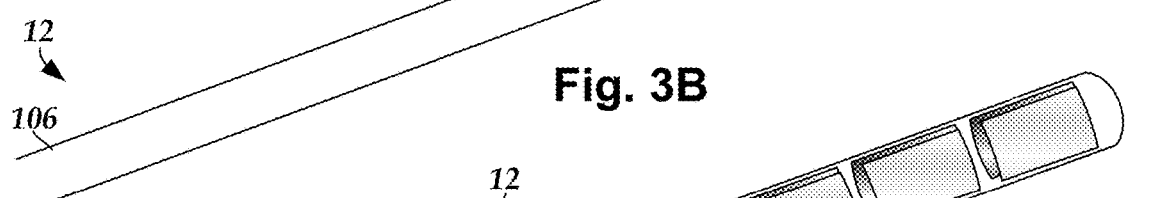
FIG. 3B is a schematic perspective view of a distal portion of another embodiment of an electrical stimulation lead with segmented electrodes.
Figure 3C:
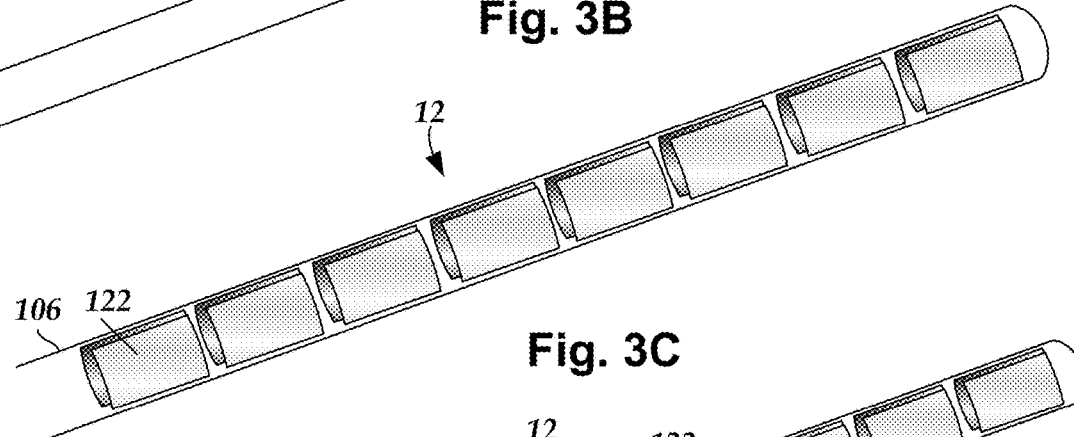
FIG. 3C is a schematic perspective view of a distal portion of a third embodiment of an electrical stimulation lead with segmented electrodes.
Figure 3D:
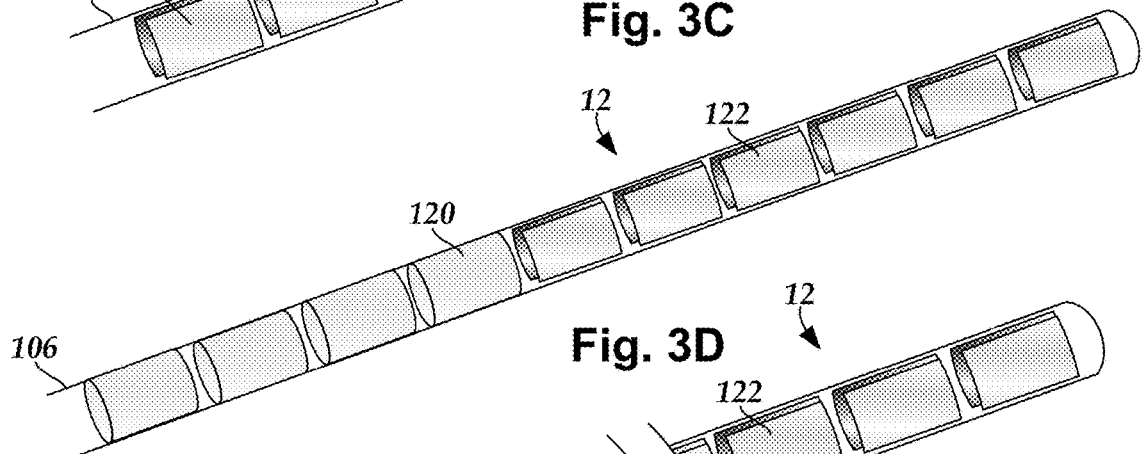
FIG. 3D is a schematic perspective view of a distal portion of a fourth embodiment of an electrical stimulation lead with segmented electrodes.
Figure 3E:
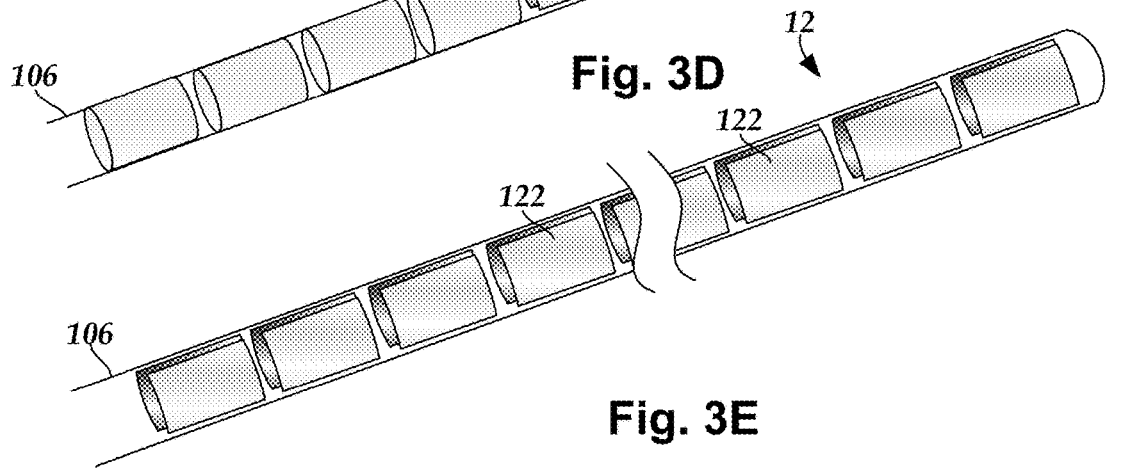
FIG. 3E is a schematic perspective view of a distal portion of a fifth embodiment of an electrical stimulation lead with segmented electrodes.

In FIGS. 3A, 3B, and 3D the electrodes are shown as including both ring electrodes 120 and segmented electrodes 122. In some embodiments, the electrodes are all segmented electrode 122, as illustrated in FIGS. 3C and 3E. The segmented electrodes 122 of FIG. 3A are in sets of three, where the three segmented electrodes of a particular set are electrically isolated from one another and are circumferentially offset along the lead 12. Any suitable number of segmented electrodes can be formed into a set including, for example, two, three, four, or more segmented electrodes. The lead 12 of FIG. 3A has thirty segmented electrodes 122 (ten sets of three electrodes each) and two ring electrodes 120 for a total of 32 electrodes.

Segmented electrodes can be used to direct stimulus current to one side, or even a portion of one side, of the lead. When segmented electrodes are used in conjunction with an implantable pulse generator that delivers current stimulus, current steering can be achieved to deliver the stimulus more precisely to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue.

FIG. 3A illustrates a 32-electrode lead 12 with a lead body 106 and two ring electrodes 120 proximal to thirty segmented electrodes 122 arranged in ten sets of three segmented electrodes each. In the illustrated embodiments, the ring electrodes 120 are proximal to the segmented electrodes 122. In other embodiments, the ring electrodes 120 can be proximal to, or distal to, or any combination thereof.

Any number of segmented electrodes 122 may be disposed on the lead body including, for example, one, two, three, four, five, six, seven, eight, nine, ten, eleven, twelve, thirteen, fourteen, fifteen, sixteen, twenty, twenty-four, twenty-eight, thirty, thirty-two, or more segmented electrodes 122. It will be understood that any number of segmented electrodes 122 may be disposed along the length of the lead body. A segmented electrode 122 typically extends only 75%, 67%, 60%, 50%, 40%, 33%, 25%, 20%, 17%, 15%, or less around the circumference of the lead.

The segmented electrodes 122 may be grouped into sets of segmented electrodes, where each set is disposed around a circumference of the lead 12 at a particular longitudinal portion of the lead 12. The lead 12 may have any number of segmented electrodes 122 in a given set of segmented electrodes. The lead 12 may have one, two, three, four, five, six, seven, eight, or more segmented electrodes 122 in a given set. The lead 12 may have any number of sets of segmented electrode including, but not limited to, one, two, three, four, five, six, eight, ten, twelve, fifteen, sixteen, twenty, or more sets. The segmented electrodes 122 may be uniform, or vary, in size and shape. In some embodiments, the segmented electrodes 122 are all of the same size, shape, diameter, width or area or any combination thereof. In some embodiments, the segmented electrodes 122 of each circumferential set (or even all segmented electrodes disposed on the lead 12) may be identical in size and shape.

Each set of segmented electrodes 122 may be disposed around the circumference of the lead body to form a substantially cylindrical shape around the lead body. The spacing between individual electrodes of a given set of the segmented electrodes may be the same, or different from, the spacing between individual electrodes of another set of segmented electrodes on the lead 12. In at least some embodiments, equal spaces, gaps or cutouts are disposed between each segmented electrode 122 around the circumference of the lead body. In other embodiments, the spaces, gaps or cutouts between the segmented electrodes 122 may differ in size or shape. In other embodiments, the spaces, gaps, or cutouts between segmented electrodes 122 may be uniform for a particular set of the segmented electrodes 122, or for all sets of the segmented electrodes 122. The sets of segmented electrodes 122 may be positioned in irregular or regular intervals along a length of the lead body.

The electrodes of the lead 12 are typically disposed in, or separated by, a non-conductive, biocompatible material of a lead body 106 including, for example, silicone, polyurethane, and the like or combinations thereof. The lead body 106 may be formed in the desired shape by any process including, for example, extruding, molding (including injection molding), casting, and the like. Electrodes and connecting wires can be disposed onto or within a lead body either prior to or subsequent to a molding or casting process. The non-conductive material typically extends from the distal end of the lead body 106 to the proximal end of the lead body 106.

FIG. 3B to 3E illustrate other embodiments of leads with segmented electrodes 122. FIG. 3B illustrates a sixteen electrode lead 12 having one ring electrode 120 that is proximal to five sets of three segmented electrodes 122 each. FIG. 3C illustrates a sixteen electrode lead 12 having eight sets of two segmented electrodes 122 each. As illustrated in FIG. 3C, an embodiment of a lead 12 does not necessarily include a ring electrode. FIG. 3D illustrates a sixteen electrode lead 12 having four ring electrodes 120 that are proximal to six sets of two segmented electrodes 122 each. FIG. 3E illustrates a thirty-two electrode lead 12 having sixteen sets of two segmented electrodes 122 each (for clarity of illustration, not all of the electrodes are shown). It will be recognized that any other electrode combination of ring electrodes, segmented electrodes, or both types of electrodes can be used.

When the lead 12 includes both ring electrodes 120 and segmented electrodes 122, the ring electrodes 120 and the segmented electrodes 122 may be arranged in any suitable configuration. For example, when the lead 12 includes two or more ring electrodes 120 and one or more sets of segmented electrodes 122, the ring electrodes 120 can flank the one or more sets of segmented electrodes 122. Alternately, the two or more ring electrodes 120 can be disposed proximal to the one or more sets of segmented electrodes 122 or the two or more ring electrodes 120 can be disposed distal to the one or more sets of segmented electrodes 122.

The electrodes 120, 122 may have any suitable longitudinal length including, but not limited to, 2, 3, 4, 4.5, 5, or 6 mm. The longitudinal spacing between adjacent electrodes 120, 122 may be any suitable amount including, but not limited to, 1, 2, or 3 mm, where the spacing is defined as the distance between the nearest edges of two adjacent electrodes. In some embodiments, the spacing is uniform between longitudinally adjacent of electrodes along the length of the lead. In other embodiments, the spacing between longitudinally adjacent electrodes may be different or non-uniform along the length of the lead.

Examples of leads with segmented electrodes include U.S. Patent Application Publications Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/0197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. A lead may also include a tip electrode and examples of leads with tip electrodes include at least some of the previously cited references, as well as U.S. Patent Application Publications Nos. 2014/0296953 and 2014/0343647, all of which are incorporated herein by reference in their entireties. A lead with segmented electrodes may be a directional lead that can provide stimulation in a particular direction using the segmented electrodes.

Although electrical stimulation of tissue has demonstrated effectiveness for many medical conditions, there can be side-effects to electrical stimulation. Multi-electrode leads may enable greater selectivity of tissue to be stimulated which may provide improved therapy, but there can be a challenge in determining which electrodes and stimulation parameters provide therapeutic benefit while reducing or eliminating side effects.

In at least some instances, a treating physician may wish to tailor the stimulation parameters (such as which one or more of the stimulating electrodes to use, the stimulation pulse amplitude (such as current or voltage amplitude depending on the stimulator being used,) the stimulation pulse width, the stimulation frequency, the duty cycle, the stimulation phase, or the like or any combination thereof) for a particular patient. Conventionally, the clinician or programmer tries different selections of electrodes, stimulation amplitude, and other parameters and then determines therapy effectiveness or side effects using visual observation, sensor observation, patient feedback, or the like. This can be a lengthy and time-consuming process.

In contrast to the conventional programming methods, as described herein, an automated (or at least partially automated) programming system or method can include the automated sequential testing of different sets of stimulation parameters and evaluation of each set of stimulation parameters using a sensor or sensed responses to the stimulation. The automated programming system or method can select one or more of the tested sets of stimulation parameters for therapy. In at least some embodiments, the automation can then be fine-tuned (or otherwise altered) by manual adjustment of the stimulation parameter by a clinician or other programmer.

Figure 4:
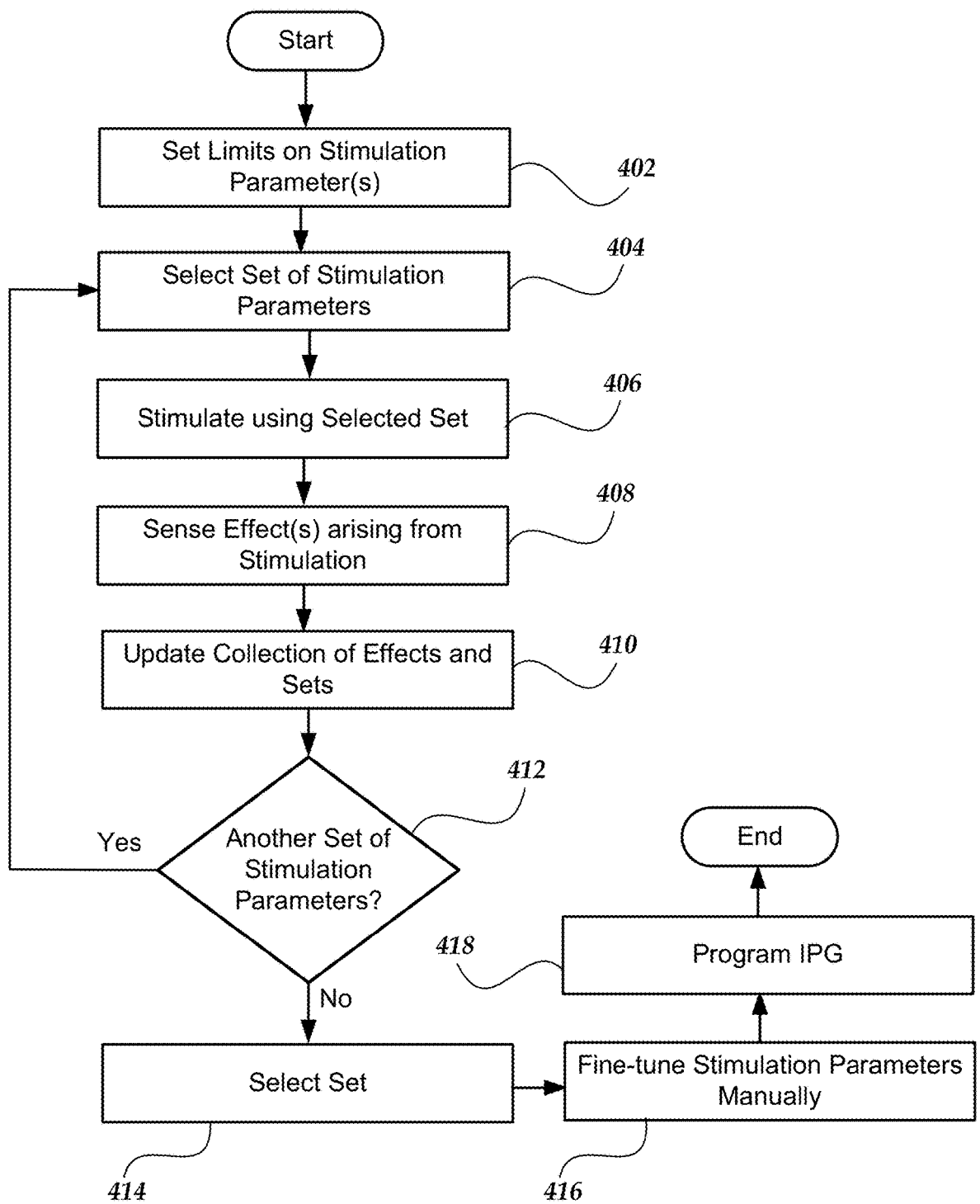
FIG. 4 is a flowchart of one embodiment of a method of determining stimulation parameters for therapy.

FIG. 4 illustrates one embodiment of a method of determining stimulation parameters for therapy. In step 402, a user, such as a clinician or other programmer, sets limits on one or more stimulation parameters. Examples of stimulation parameters that can be limited include, but are not limited to, amplitude, electrode selection, stimulation direction, pulse width, pulse frequency, or the like or any combination thereof. For example, the user may place a lower limit on the amplitude because lower amplitudes are unlikely to produce satisfactory effects or the user may place an upper limit because higher amplitudes are likely to produce side effects. The user may place limits on which electrodes are selected on the lead (for example, electrodes 2 to 5 in an eight-electrode array) so that only electrodes that are near the target region are selected. For leads with segmented electrodes, the user may limit the direction of the stimulation so that only certain segmented electrodes (within those limits on direction) will be tested. This may reflect knowledge of the position and orientation of the lead in the tissue and the desired target region for stimulation.

Steps 404 to 412 form a loop in which a processor automatically tests multiple sets of stimulation parameters, constrained by the limits set in step 402, and determines the effect(s) of the test stimulations. The effect(s) can be therapeutic effect(s) or side effect(s) or any combination thereof. In at least some embodiments, the loop is closed and occurs automatically. In at least some embodiments, the loop may occur with no manual input. In at least some embodiments, the loop may occur with manual input limited to input from the clinician, programmer, or patient regarding observed therapeutic or side effects. In at least some embodiments, the loop can be halted manually by the user, clinician, programmer, patient, or any combination thereof. This manual control can be used, for example, to halt the process if there are safety or patient comfort concerns or issues. In at least some embodiments, the processor may also include one or more thresholds (for example, threshold values of side effects) that, when met or exceeded, may halt the loop as well. In at least some embodiments, halting the loop based on one or more thresholds can result from the sensing of therapeutic or side effects described below.

In step 404, a set of stimulation parameters is selected. In at least some embodiments, one or more (or even all of the) sets of stimulation parameters that are to be tested are determined prior to the start of the initial loop of steps 404 to 412. In at least some embodiments, additional sets of stimulation parameters may be determined during, or as a result of, the loop of steps 404 to 412 based, for example, on the effect(s) sensed during the testing. Non-limiting examples of procedures for determining sets of parameters based on feedback or sensed effects are described in U.S. Pat. No. 10,603,498, which is incorporated herein by reference in its entirety.

In at least some embodiments, the testing of the sets of stimulation parameters can be performed according to a predefined routine or order. For example, the predefined routine or order for testing different electrode selections may start at a proximal position and move distally for each subsequent set or start at a distal position and move proximally for each subsequent set. A predefined routine or order for testing different amplitudes may start at a low or intermediate amplitude and increase for each subsequent set.

In other embodiments, the testing of the sets of stimulation parameters can be performed in any other suitable order including random, pseudo-random, partially random, or based on any other selection method or criterion/criteria.

In at least some embodiments, the testing of the sets of stimulation parameters can be performed using coarse testing of sets that differ in one parameter, followed by fine-tuning for that parameter, and then proceeding to do the same for one or more additional parameters. Examples of methods for testing the sets of stimulation parameters are presented below in the embodiments illustrated in FIG. 5.

In step 406, the patient is stimulated using the selected set of stimulation parameters. In step 408, one or more effects of the stimulation are sensed. Any suitable therapeutic effects, side effects, response effects, or any combination thereof can be sensed. A response effect can be any effect that is a result of the stimulation and can include, but are not limited to, therapeutic (e.g., beneficial) effects or side (e.g., detrimental) effects. Such response effects can be, for example, neural response such as an evoked compound action potential (ECAP), an evoked resonant neural activity (ERNA), or a local field potential (LFP). These response effects are not necessarily therapeutic or side effects.

In at least some embodiments, one or more effects are sensed by a sensor external to the IPG, by a sensor coupled to the IPG, or by one or more of the electrodes of the leads (acting as sensor(s)), or the like or any combination thereof. In at least some embodiments, the sensor or electrodes are used to obtain measurements of the effect(s). In at least some embodiments, the IPG, CP, RC, ETS, or other device are used to evaluate the measurements from the sensor or electrodes. Examples of methods for sensing the effect(s) are presented below including the embodiments illustrated in FIG. 6, as well as in U.S. Pat. Nos. 10,357,657; 10,369,364; and 10,716,505 and U.S. Patent Application Publications Nos. 2014/0243926; 2014/0276707; 2014/0277282; 2020/0376263; 2020/0398057; and 2021/0023374, all of which are incorporated herein by reference in their entireties.

In at least some embodiments, the valuation of the measurements from the sensor or electrodes can include a comparative evaluation of the therapeutic effect(s) and side effect(s). In at least some embodiments, an intensity or benefits scale can be used to rate the therapeutic effect(s) and an intensity or detriment scale can be used to rate the side effect(s). In at least some embodiments, these two scales can be selected for comparison. For example, in a least some embodiments, a therapeutic score may be determined by subtracting the rating for the side effect(s) from the rating for the therapeutic effect(s). The higher the therapeutic score, the likelihood that the corresponding stimulation is beneficial. Other algorithms or methods of comparing the therapeutic effect(s) to the side effect(s) can be used.

Figure 7:
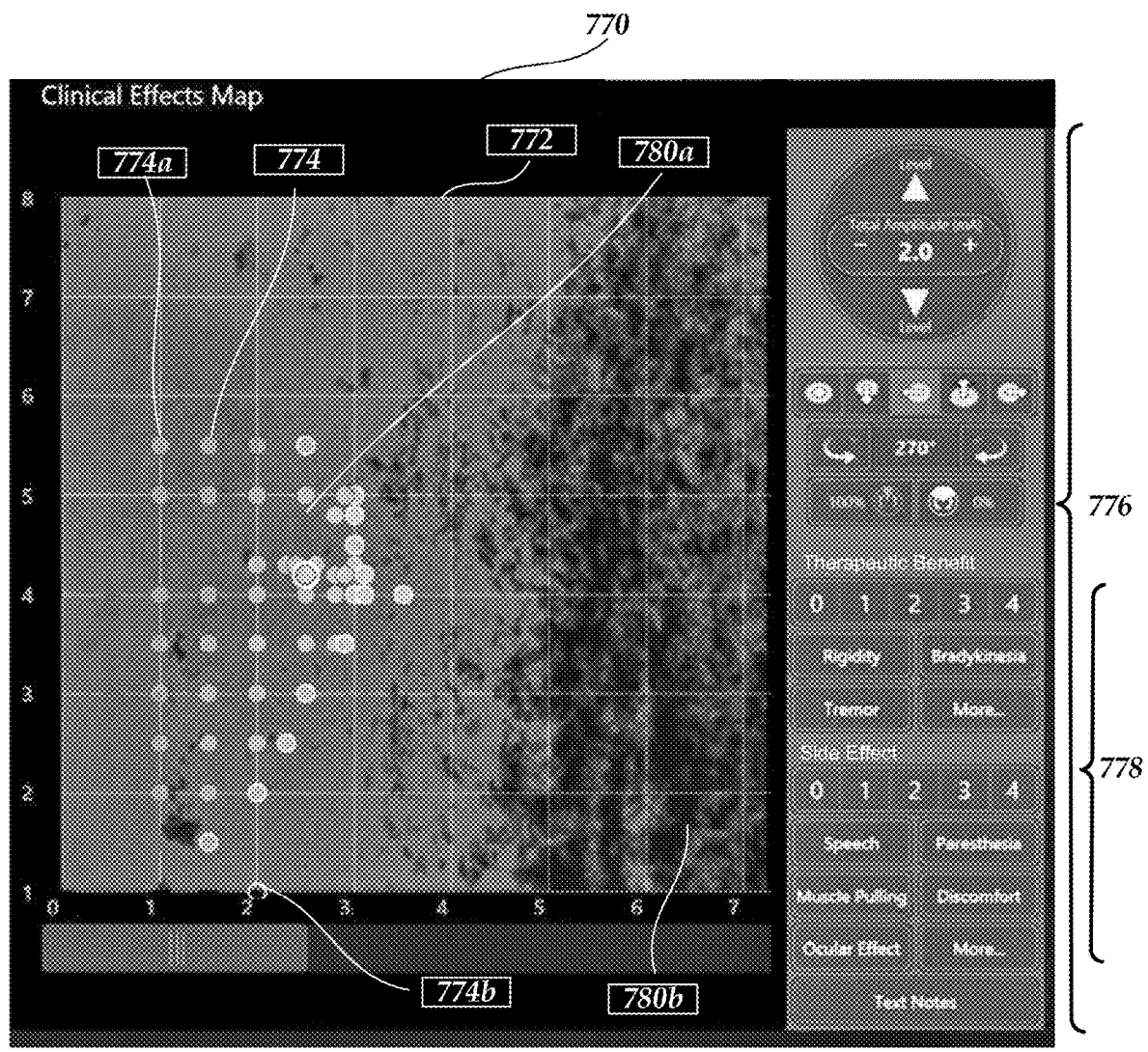
FIG. 7 is a schematic illustration of one embodiment of a user interface with a clinical effects map.

In step 410, a collection of the effects and sets of stimulation parameters are updated with the current set of stimulation parameters and the sensed effect(s). The collection can be in any suitable form including, but not limited to, a database, a clinical effects map or graph, or the like or any combination thereof. FIG. 7 illustrates one embodiment of a clinical effects map. Additional information regarding clinical effects maps can be found in, for example, U.S. Pat. Nos. 9,227,074; 9,248,296; 9,358,398; 9,474,903; 10,603,498; and 10,071,249 and U.S. Patent Application Publication No. 2018/0264278, all of which are incorporated herein in their entireties.

FIG. 7 illustrates one embodiment of a user interface 770 that includes a clinical effects map 772 that maps the electrode position along the y-axis and stimulation amplitude (in mA) along the x-axis. Examples of three-dimensional clinical effects maps and clinical effects maps using cylindrical coordinates (for example, where rho represent amplitude, phi represents a rotational angle, and z represents electrode position) are presented in the references cited above. Positions on the clinical effects map 772 correspond to stimulations, each associated with activation of an actual or virtual electrode at a particular stimulation amplitude. The virtual electrodes can correspond to stimulation using a combination of actual electrodes. For example, a position between electrode 1 and electrode 2 can correspond to stimulation using a combination of electrodes 1 and 2 (for example, 50% of the stimulation amplitude on electrode 1 and 50% of the stimulation amplitude on electrode 2 to provide a virtual electrode with a midpoint between electrodes 1 and 2).

In the illustrated embodiment, the markings 774 on the clinical effects map 772 correspond to actual stimulation events. In at least some embodiments, the markings 774 may also provide information about the effect(s) produced by the stimulation. In the illustrated embodiment of FIG. 7, the markings can have a circle 774*a* that corresponds to therapeutic effect(s) with variation in color or intensity indicating the strength of the therapeutic effect(s). The markings can have a ring 774*b* that corresponds to side effect(s) with variation in color or intensity indicating the strength of the side effect(s). In the illustrated embodiment, the user interface 770 includes an input section 776 with controls 778 for inputting specific types of therapeutic or side effects and corresponding intensities.

The clinical effects map 772 may also include a feature that indicates potential target regions 780*a* and potential avoidance regions 780*b* that are determined based on the preceding stimulation instances. For example, the potential target regions 780*a* can be indicated on the clinical effects map 772 as a particular background color (for example, green) and correspond to regions near stimulation instances in which the therapeutic effect(s) are greater than the side effect(s) (and, optionally, where the side effect(s) are below a threshold level). The potential avoidance regions 780*b* can be indicated on the clinical effects map 772 as a different background color (for example, red) and correspond to regions where the trendlines from the preceding stimulation instances indicate that the side effect(s) are likely greater than the therapeutic effect(s) or where the side effects are likely to meet or exceed a threshold level. The potential avoidance region 780*b* may also include the region out the limits set by the user in step 402, as described above.

In step 412, the processor determines if there is another set of stimulation parameters to test. If yes, then the method returns to step 404. If no, then the method continues.

In step 414, the processor selects one of the sets of stimulation parameters based on the testing. In at least some embodiments, the set of stimulation parameters with the best therapeutic response is selected. In at least some embodiments, the processor will select the set of stimulation parameters based on both the therapeutic response and the presence or severity of side effects. In at least some embodiments, the ratings of the therapeutic effect(s), side effect(s), or any combination thereof can be used to select the set of stimulation parameters. In at least some embodiments, the therapeutic scores (e.g., the different between the rating for the therapeutic effect(s) and the rating for the side effect(s)) for the sets of stimulation parameters can be used to select the set of stimulation parameters.

In optional step 416, a clinician or programmer can fine-tune the stimulation parameters by altering or modifying the set of stimulation parameters selected by the processor in step 414. In at least some embodiments, the processor may require that the clinician or programmer authorize or accept the selected set of stimulation parameters. In step 418, the IPG is programmed using the selected set of stimulation parameters or the set of stimulation parameters after modification or alteration by the clinician or programmer in step 416.

In at least some embodiments, steps 404 to 412 can be performed while the patient is asleep when the testing is performed without patient or clinician feedback. In at least some embodiments, the method can result in personalized therapy for the patient or can provide programming that is tailored to the patient's physiological response.

In at least some embodiments, the method can be performed periodically and can be used to track disease progression over time. In at least some embodiments, the method can be performed periodically to adjust stimulation parameters or to improve closed-loop device operation.

Figure 5:
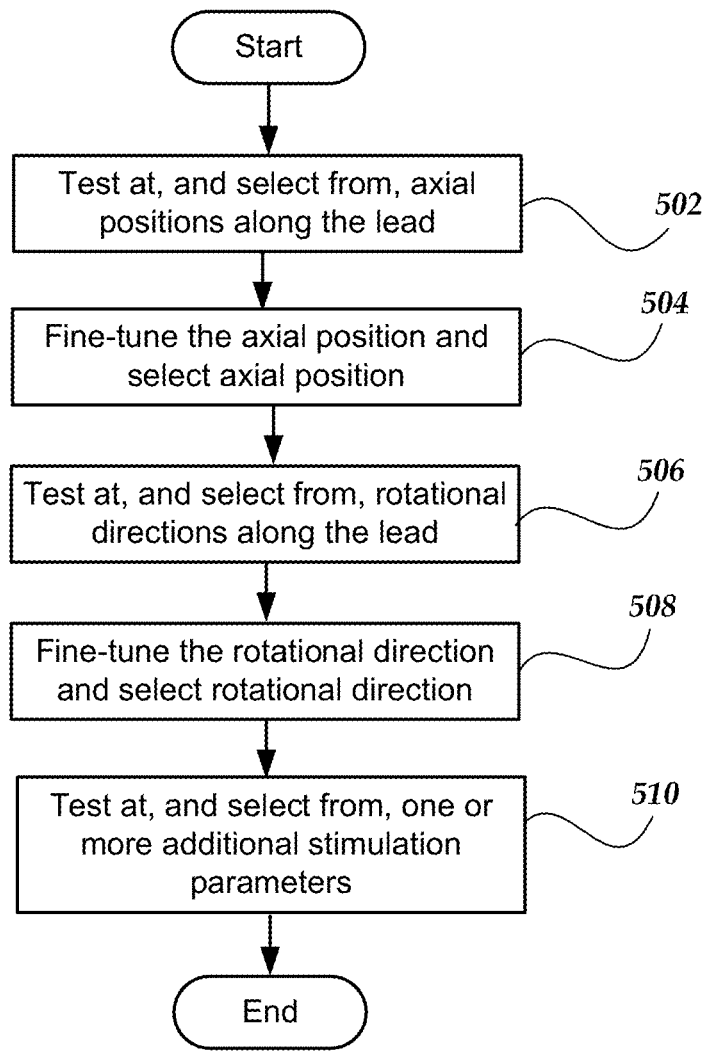
FIG. 5 is a flowchart of one embodiment of a method for selection of a set of stimulation parameters.

One embodiment of a method for selection of a set of stimulation parameters is illustrated in FIG. 5. In step 502, a number (for example, two, three, four, five, six, eight, ten, twelve, or more) of different axial positions along the lead are tested. Each of the axial positions can correspond to a single electrode (or a set of segmented electrodes at the same axial position along the lead) or to multiple electrodes (including multiple electrodes at different axial positions along the lead to provide a virtual electrode that is a combination of these electrodes.) As an example, an axial position between electrode 1 (or a set of segmented electrodes at axial position 1 along the lead) and electrode 2 (or a set of segmented electrodes at axial position 2 along the lead) can correspond to stimulation using a combination of electrodes 1 and 2. For example, an axial position of 1.5 may correspond to 50% of the stimulation amplitude on electrode 1 and 50% of the stimulation amplitude on electrode 2 and an axial position of 1.25 may correspond to 75% of the stimulation amplitude on electrode 1 and 25% of the stimulation amplitude on electrode 2.

In at least some embodiments, the different axial positions are selected to be uniformly spread along the portion of the lead that is permitted for use. In at least some embodiments, when a particular axial position produces side effects over a threshold level or produces therapeutic effects below a particular threshold, other axial positions near, distal, or proximal to the particular axial position may be precluded from testing. The processor may determine that the precluded axial positions may produce side effects or not produce substantial therapeutic effects.

The processor selects one or more of these initial axial positions for proceeding. For example, the processor may use a comparative evaluation of the therapeutic effect(s) and side effect(s). In at least some embodiments, an intensity or benefits scale can be used to rate the therapeutic effect(s) and an intensity or detriment scale can be used to rate the side effect(s). In at least some embodiments, these two scales can be selected for comparison. For example, in a least some embodiments, a therapeutic score may be determined by subtracting the rating for the side effect(s) from the rating for the therapeutic effect(s). The higher the therapeutic score, the likelihood that the corresponding stimulation is beneficial. Other algorithms or methods of comparing the therapeutic effect(s) to the side effect(s) can be used.

In optional step 504, the processor may fine-tune the axial position by testing additional axial positions near the selected initial axial positions. For example, if the axial position corresponding to electrode 3 (or a set of segmented electrodes at axial position 3 along the lead) is selected, then fine-tuning may include testing sets of stimulation parameters with axial positions in the range of 2 to 4 (e.g., 2.25, 2.5, 2.75, 3.25, 3.5, and 3.75) which corresponds axial positions within one axial electrode spacing of axial position 3. In at least some embodiments, the fine-tuning includes testing axial positions within one, two, three, or four or more axial electrode spacings from the selected initial axial position. The processor then selects one or more these fine-tuned axial positions (or the initial axial positions) for proceeding using any suitable method including those described above.

In optional step 506, when the selected initial or fine-tuned axial positions include segmented electrodes, the processor can select two or more different rotational directions at the selected axial positions. Each of the rotational directions can correspond to a single segmented electrode or to multiple segmented electrodes (including multiple segmented electrodes at different axial positions along the lead to provide a virtual electrode that is a combination of these segmented electrodes.) As an example, a rotational direction between segmented electrode 1 and segmented electrode 2 can correspond to stimulation using a combination of segmented electrodes 1 and 2. For example; a rotational direction of 1.5 may correspond to 50% of the stimulation amplitude on segmented electrode 1 and 50% of the stimulation amplitude on segmented electrode 2.

The processor selects one or more of these initial rotational directions for proceeding. In optional step 508, the processor can also fine-tune the rotational direction(s) by testing additional rotational directions near the selected initial rotational direction. For example, if the rotational direction corresponding to electrode 2 is selected, then fine-tuning may include testing sets of stimulation parameters with rotational directions in the range of 1 to 3 (e.g., 1.25, 1.5, 1.75, 2.25, 2.5, and 2.75). In at least some embodiments, the fine-tuning includes testing rotational directions within 120, 100, 90, 60, 45, or fewer degrees from the selected initial rotational direction. One of the fine-tuned rotational directions (or initial rotational direction(s)) can be selected for proceeding using any suitable method including those described above.

In step 510, one or more additional stimulation parameters can be tested using the selected axial position and optional rotational direction. For example, different stimulation amplitudes can be tested. Other stimulation parameters can include pulse duration, pulse frequency, or the like or any combination thereof. For each of these one or more additional stimulation parameters, a value can be selected based on the testing using any suitable method including those described above.

Figure 6:
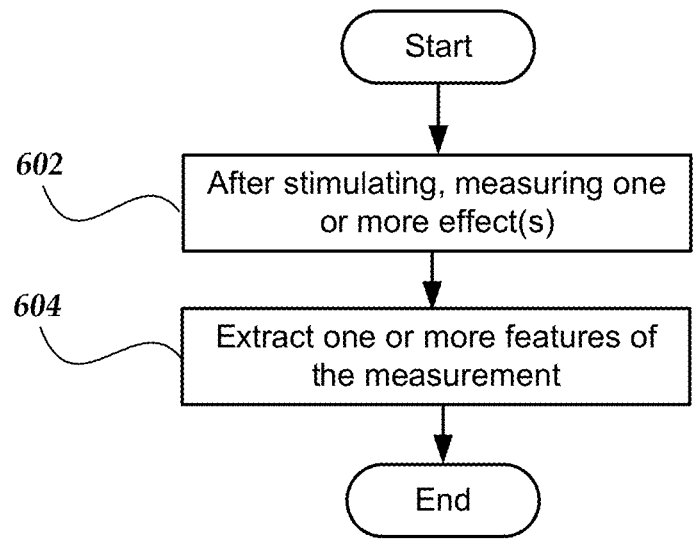
FIG. 6 is a flowchart of one embodiment of a method of sensing a stimulation effect.

One embodiment of a method of sensing a stimulation effect is provided in FIG. 6. In step 602, after stimulating with a set of stimulation parameters, the sensor makes a measurement of one or more effect(s) of the stimulation including, but not limited to, therapeutic effects, side effects, response effects, or the like or any combination thereof. The stimulation effect can be, for example, an evoked compound action potential (ECAP), an evoked resonant neural activity (ERNA), a local field potential (LFP), or the like or any combination thereof. In some embodiments, the stimulation effect can be an effect of the disease or disorder such as rigidity, tremor, impaired or unwanted movement, synchronized signals in the brain or elsewhere, seizures, or the like or any combination thereof. The sensor can be, for example, a sensor external to the IPG, by a sensor coupled to the IPG, or by one or more of the electrodes of the leads (acting as sensor(s)), or the like or any combination thereof. In at least some embodiments, there may be at least some digital signal processing of the measurement in step 602, such as, for example, finite impulse response (FIR) filtering or recursively averaging epochs of data.

Figure 8:
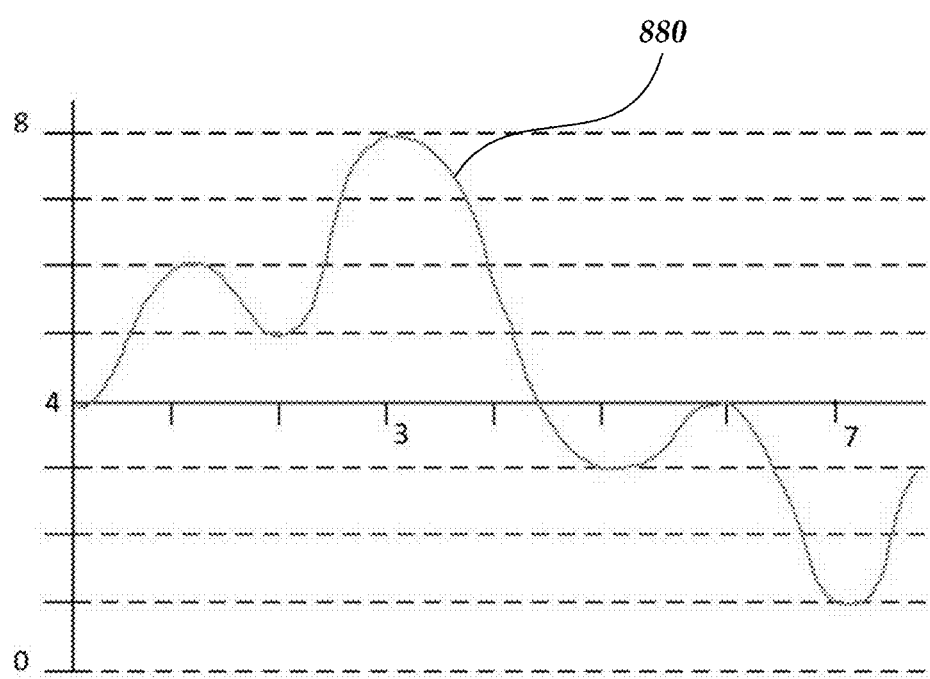
FIG. 8 is schematic illustration of one embodiment of a signal measured using a sensor in response to stimulation.

In step 604, one or more features of the measurements are extracted. For example, in at least some embodiments, the measurements can be signal that is recorded over time and one or more features of the signal can be extracted. FIG. 8 illustrates one embodiment of a signal 880 measured using a sensor (such as an external or internal sensor or one or more of the electrodes of the lead.) In FIG. 8, the signal 880 is presented as a graph of current (or voltage) amplitude (y-axis) versus time (x-axis). Examples of the measurement of such signals 880 can be found at, for example, U.S. Pat. Nos. 10,357,657; 10,369,364; and 10,716,505 and U.S. Patent Application Publications Nos. 2014/0243926; 2014/0276707; 2014/0277282; 2020/0376263; 2020/0398057; and 2021/0023374, all of which are incorporated herein by reference in their entireties.

Non-limiting examples of features that can be extracted from the signal 880 include, for example, the range of amplitude, value(s) of positive peaks, value(s) of negative peaks, area under the signal curve, length of the signal curve, or the like or any combination thereof. In at least some embodiments, a range of time is selected or predefined for the extraction of the feature(s). For example, the range of time may be a block of 64, 128, 256, or 512 (or any other suitable number) of samples of the measurements made by the sensor.

Signal 880 of FIG. 8 can be used as an example, to illustrated different measurements. For example, a y-range measurement can correspond to $y_{max}-y_{min}$ which in the case of signal 880 is 8−1=7. An x-range measurement can correspond, for example, to the x-range between $y_{max}$ (e.g., $x_{y\text{-}max}$=3 for signal 880) and $x_{min}$ (e.g., $x_{y\text{-}min}$=7 for signal 880) which in the case of signal 880 is (7−3=4).

Another example is the area under the curve of the signal. This area can be determined using any suitable method including integration techniques or the like. One example uses the algorithm Area Under Curve=$\Sigma|y|$ at each value of x which for signal 880 is 6+5+8+6+3+4+1=33.

Yet another example, is the length of the curve of the signal. This length can be determined using any suitable method for determining or estimating a length of a curve. One example uses the algorithm Curve Length=$\Sigma|\Delta y|=\Sigma\beta|y_i-y_{i-1}|$ which for signal 880 is 2+1+3+2+3+1+3=15.

The methods, techniques, and systems described herein are presented in the context of an electrical stimulation system, but it will be recognized that these methods, techniques, and systems can be used with an optical stimulation system or an electrical/optical stimulation system. Examples of optical stimulation systems or electrical/optical stimulation systems are found in U.S. Patent Application Publications Nos. 2013/0317572; 2013/0317573; 2017/0259078; 2017/0225007; 2018/0110971; 2018/0369606; 2018/0369607; 2019/0209849; 2019/0209834; 2020/0094047; and 2020/0155854 and U.S. patent application Ser. No. 16/883,404, all of which are incorporated herein by reference in their entireties.

It will be understood that each block of the flowchart illustration, and combinations of blocks in the flowchart illustration and methods disclosed herein, can be implemented by computer program instructions. These program instructions may be provided to a processor to produce a machine or engine, such that the instructions, which execute on the processor, create means for implementing the actions specified in the flowchart block or blocks or engine disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device. The computer program instructions can be stored locally or nonlocally (for example, in the Cloud).

The above specification and examples provide a description of the arrangement and use of the invention. Since many embodiments of the invention can be made without departing from the spirit and scope of the invention, the invention also resides in the claims hereinafter appended.

What is claimed as new and desired to be protected is:

1. A method for automating selection of stimulation parameters for a stimulation device implanted in a patient, the method comprising:
    setting, by a user, at least one limit on each of at least three stimulation parameters, each of the at least three stimulation parameters being different and selected from an axial position along an electrical stimulation lead, a rotational direction of stimulation, a stimulation amplitude, a pulse duration, a pulse frequency, or a duty cycle, wherein each of the at least one limit comprises an upper limit, a lower limit, a limit on electrode selection, or a limit on stimulation direction; and
    performing, automatically using at least one processor, the following actions sequentially and individually for each of the at least three stimulation parameters constrained by the at least one limit, wherein the actions are fully performed with respect to one of the at least three stimulation parameters before performing the actions for another one of the at least three stimulation parameters:
        selecting a one of the at least three stimulation parameters,
        stimulating tissue of the patient, by the stimulation device, using different first values for the selected one of the at least three stimulation parameters constrained by the at least one limit for the one of the at least three stimulation parameters,
        for each of the different first values, sensing one or more first effects arising in response to the corresponding stimulation including sensing a signal from the stimulated tissue, wherein the signal is an evoked compound action potential (ECAP), evoked resonant neural activity (ERNA), or local field potential (LFP), wherein at least one of the one or more first effects is a feature of the signal over a selected range of time, wherein the feature comprises at least one of a range of amplitude of the signal over the selected range of time, an amount of time between a maximum amplitude of the signal and a minimum amplitude of the signal for the selected range of time, an area under a curve of the signal for the selected range of time, or a length of the curve of the signal for the selected range of time,
        updating, by the at least one processor and for each of the different first values, a collection of effects and corresponding values of the at least three stimulation parameters with the one or more first effects and the corresponding different first values of the one of the at least three stimulation parameters,
        selecting, by the processor, a coarse value from the different first values of the one of the at least three stimulation parameters based on the sensed one or more first effects,
        stimulating tissue of the patient, by the stimulation device, using different second values for the selected one of the at least three stimulation parameters that are within a predefined relative range around the selected coarse value of the one of the at least three stimulation parameters constrained by the at least one limit for the one of the at least three stimulation parameters,
        for each of the different second values, sensing one or more second effects arising in response to the stimulation including sensing a signal from the stimulated tissue, wherein the signal is an evoked compound action potential (ECAP), evoked resonant neural activity (ERNA), or local field potential (LFP), wherein at least one of the one or more second effects is a feature of the signal over a selected range of time, wherein the feature comprises at least one of a range of amplitude of the signal over the selected range of time, an amount of time between a maximum amplitude of the signal and a minimum amplitude of the signal for the selected range of time, an area under a curve of the signal for the selected range of time, or a length of the curve of the signal for the selected range of time,
        updating, by the at least one processor and for each of the different second values, a collection of effects and corresponding values of the at least three stimulation parameters with the one or more second effects and the corresponding different second values of the one of the at least three stimulation parameters, and
        selecting, by the processor, a fine-tuned value from the different second values of the one of the at least three stimulation parameters based on the sensed one or more second effects,
    wherein, after the fine-tuned value is selected for any one of the at least three stimulation parameters, that fine-tuned value is used in subsequent stimulations when performing the actions for another one of the at least three stimulation parameters.

2. The method of claim 1, further comprising, after selecting the fine-tuned value of the one of the at least three stimulation parameters, further fine-tuning, manually by the user, to obtain a manual fine-tuned value for one of the at least three stimulation parameters.

3. The method of claim 1, further comprising programming the stimulation device with the selected fine-tuned values for each of the at least three stimulation parameters.

4. The method of claim 1, wherein the signal is an evoked compound action potential (ECAP) or an evoked resonant neural activity (ERNA).

5. The method of claim 1, wherein the at least three stimulation parameters comprises a first stimulation parameter corresponding to an axial location along the electrical stimulation lead.

6. The method of claim 5, wherein the predefined relative range is one axial electrode spacing on both sides of the selected coarse value of the axial location.

7. The method of claim 5, wherein the at least three stimulation parameters comprises a second stimulation parameter corresponding to a rotational direction around the electrical stimulation lead.

8. The method of claim 7, wherein the predefined relative range is 120 degrees on both sides of the selected coarse value of the rotational direction.

9. The method of claim 7, wherein the at least three stimulation parameters comprises a third stimulation parameter corresponding to a stimulation amplitude.

10. A system for selection of stimulation parameters for a stimulation device implanted in a patient, the system comprising:
    at least one processor configured to perform actions, the actions comprising:

receiving, from a user, at least one limit for each of at least three stimulation parameters, each of the at least three stimulation parameters being different and selected from an axial position along an electrical stimulation lead, a rotational direction of stimulation, a stimulation amplitude, a pulse duration, a pulse frequency, or a duty cycle, wherein each of the at least one limit comprises an upper limit, a lower limit, a limit on electrode selection, or a limit on stimulation direction; and performing the following actions sequentially and individually for each of the at least three stimulation constrained by the at least one limit, wherein the actions are fully performed with respect to one of the at least three stimulation parameters before performing the actions for another one of the at least three stimulation parameters:

selecting a one of the at least three stimulation parameters, directing the stimulation device to stimulate tissue of the patient using different first values for the selected one of the at least three stimulation parameters constrained by the at least one limit for the one of the at least three stimulation parameters, for each of the different first values, sensing one or more first effects arising in response to the corresponding stimulation including sensing a signal from the stimulated tissue, wherein the signal is an evoked compound action potential (ECAP), evoked resonant neural activity (ERNA), or local field potential (LFP), wherein at least one of the one or more effects is a feature of the signal over a selected range of time, wherein the feature comprises at least one of a range of amplitude of the signal over the selected range of time, an amount of time between a maximum amplitude of the signal and a minimum amplitude of the signal for the selected range of time, an area under a curve of the signal for the selected range of time, or a length of the curve of the signal for the selected range of time, updating, for each of the different first values, a collection of the effects and corresponding values of the at least three stimulation parameters with the one or more first effects and the corresponding different first values of the one of the at least three stimulation parameters, selecting a coarse value from the different first values of the one of the at least three stimulation parameters based on the sensed one or more first effects, directing stimulation of tissue of the patient, by the stimulation device, using different second values for the selected one of the at least three stimulation parameters that are within a predefined relative range around the selected coarse value of the one of the at least three stimulation parameters constrained by the at least one limit for the one of the at least three stimulation parameters, for each of the different second values, sensing one or more second effects arising in response to the stimulation including sensing a signal from the stimulated tissue, wherein the signal is an evoked compound action potential (ECAP), evoked resonant neural activity ERNA), or local field potential (LFP), wherein at least one of the one or more second effects is a feature of the signal over a selected range of time, wherein the feature comprises at least one of a range of amplitude of the signal over the selected range of time, an amount of time between a maximum amplitude of the signal and a minimum amplitude of the signal for the selected range of time, an area under a curve of the signal for the selected range of time, or a length of the curve of the signal for the selected range of time, updating, by the at least one processor and for each of the different second values, a collection of effects and corresponding values of the at least three stimulation parameters with the one or more second effects and the corresponding different second values of the one of the at least three stimulation parameters, and selecting, by the processor, a fine-tuned value from the different second values of the one of the at least three stimulation parameters based on the sensed one or more second effects, wherein, after the fine-tuned value is selected for any one of the at least three stimulation parameters, that fine-tuned value is used in subsequent stimulations when performing the actions for another one of the at least three stimulation parameters.

11. The system of claim 10, further comprising the stimulation device.

12. The system of claim 11, wherein the stimulation device comprises the electrical stimulation lead having electrodes disposed along a distal portion of the electrical stimulation lead.

13. The system of claim 12, wherein sensing one or more first effects comprising sensing the one or more first effects arising in response to the stimulation using at least one of the electrodes of the electrical stimulation lead.

14. The system of claim 10, further comprising a sensor external to the stimulation device, wherein sensing one or more first effects comprising sensing the one or more first effects arising in response to the stimulation using the sensor.

15. The system of claim 10, wherein the actions further comprise programming the stimulation device with the fine-tuned values selected for the at least three stimulation parameters.

16. A non-transitory computer-readable medium having stored thereon instructions for execution by at least one processor, the instructions comprising:

a) receiving, from a user, at least one limit for each of at least three stimulation parameters, each of the at least three stimulation parameters being different and selected from an axial position along an electrical stimulation lead, a rotational direction of stimulation, a stimulation amplitude, a pulse duration, a pulse frequency, or a duty cycle, wherein each of the at least one limit comprises an upper limit, a lower limit, a limit on electrode selection, or a limit on stimulation direction; and b) performing the following actions sequentially and individually for each of the at least three stimulation constrained by the at least one limit, wherein the actions are fully performed with respect to one of the at least three stimulation parameters before performing the actions for another one of the at least three stimulation parameters:

selecting a one of the at least three stimulation parameters, directing the stimulation device to stimulate tissue of the patient using different first values for the selected one of the at least three stimulation parameters constrained by the at least one limit for the one of the at least three stimulation parameters, for each of the different first values, sensing one or more first effects arising in response to the corresponding stimulation including sensing a signal from the stimulated tissue, wherein the signal is an evoked compound action potential (ECAP), evoked resonant neural activity (ERNA), or local field potential (LFP), wherein at least one of the one or more effects is a feature of the signal over a selected range of time, wherein the feature comprises at least one of a range of amplitude of the signal over the selected range of time, an amount of time between a maximum amplitude of the signal and a minimum amplitude of the signal for the selected range of time, an area under a curve of the signal for the selected range of time, or a length of the curve of the signal for the selected range of time, updating, for each of the different first values, a collection of the effects and corresponding values of the at least three stimulation parameters with the one or more first effects and the corresponding different first values of the one of the at least three stimulation parameters, selecting a coarse value from the different first values of the one of the at least three stimulation parameters based on the sensed one or more first effects, directing stimulation of tissue of the patient, by the stimulation device, using different second values for the selected one of the at least three stimulation parameters that are within a predefined relative range around the selected coarse value of the one of the at least three stimulation parameters constrained by the at least one limit for the one of the at least three stimulation parameters, for each of the different second values, sensing one or more second effects arising in response to the stimulation including sensing a signal from the stimulated tissue, wherein the signal is an evoked compound action potential (ECAP), evoked resonant neural activity (ERNA), or local field potential (LFP), wherein at least one of the one or more second effects is a feature of the signal over a selected range of time, wherein the feature comprises at least one of a range of amplitude of the signal over the selected range of time, an amount of time between a maximum amplitude of the signal and a minimum amplitude of the signal for the selected range of time, an area under a curve of the signal for the selected range of time, or a length of the curve of the signal for the selected range of time, updating, by the at least one processor and for each of the different second values, a collection of effects and corresponding values of the at least three stimulation parameters with the one or more second effects and the corresponding different second values of the one of the at least three stimulation parameters, and selecting, by the processor, a fine-tuned value from the different second values of the one of the at least three stimulation parameters based on the sensed one or more second effects, wherein, after the fine-tuned value is selected for any one of the at least three stimulation parameters, that fine-tuned value is used in subsequent stimulations when performing the actions for another one of the at least three stimulation parameters.

17. The non-transitory computer-readable medium of claim 16, wherein the instructions further comprise, after selecting the fine-tuned value of the one of the at least three stimulation parameters, further fine-tuning, manually by the user, to obtain a manual fine-tuned value for one of the at least three stimulation parameters.

18. The non-transitory computer-readable medium of claim 16, wherein the instructions further comprising repeating the instruction b) periodically to track disease progression over time.

* * * * *